(12) United States Patent
Ankenbauer et al.

(10) Patent No.: US 7,030,220 B1
(45) Date of Patent: Apr. 18, 2006

(54) THERMOSTABLE ENZYME PROMOTING THE FIDELITY OF THERMOSTABLE DNA POLYMERASES-FOR IMPROVEMENT OF NUCLEIC ACID SYNTHESIS AND AMPLIFICATION IN VITRO

(75) Inventors: Waltraud Ankenbauer, Penzberg (DE); Frank Laue, Paehl-Fischen (DE); Harald Sobek, Penzberg (DE); Michael Greif, Lenggries (DE)

(73) Assignees: Roche Diagnostics GmbH, Mannheim (DE); Roche Molecular Systems Inc., Alameda, CA (US)

( * ) Notice: Subject to any disclaimer, the term of this patent is extended or adjusted under 35 U.S.C. 154(b) by 485 days.

(21) Appl. No.: 09/856,850

(22) PCT Filed: Sep. 27, 2000

(86) PCT No.: PCT/EP00/09423

§ 371 (c)(1),
(2), (4) Date: Sep. 19, 2001

(87) PCT Pub. No.: WO01/23583

PCT Pub. Date: Apr. 5, 2001

(30) Foreign Application Priority Data

Sep. 28, 1999 (EP) .................................. 99119268

(51) Int. Cl.
*C07K 1/00* (2006.01)
*C12Q 1/68* (2006.01)
*C12P 19/34* (2006.01)
*C07H 21/04* (2006.01)

(52) U.S. Cl. .......................... 530/350; 435/6; 435/91.1; 435/91.2; 536/23.1; 536/24.3; 536/24.33

(58) Field of Classification Search ................ 435/6, 435/91.1, 91.2, 183; 536/23.1, 24.3, 24.33; 530/300, 350, 388.21; 930/240
See application file for complete search history.

(56) References Cited

U.S. PATENT DOCUMENTS

| 5,391,480 A | * | 2/1995 | Davis et al. ................ 435/6 |
| 2003/0049634 A1 | * | 3/2003 | Barnes ...................... 435/6 |
| 2003/0119150 A1 | * | 6/2003 | Ankenbauer et al. ...... 435/91.2 |

FOREIGN PATENT DOCUMENTS

| DE | 198 10 879 | 9/1999 |
| EP | 0 669 401 | 8/1995 |
| EP | 0 744 470 | 11/1996 |
| EP | 0 870 832 | 10/1998 |
| EP | 1 088 891 | 4/2001 |
| WO | WO 94 23066 | 10/1994 |
| WO | WO 9423066 A1 * | 10/1994 |
| WO | WO 94 26766 | 11/1994 |
| WO | WO 98 45452 | 10/1998 |
| WO | WO 99 13060 | 3/1999 |
| WO | WO 00 68411 | 11/2000 |
| WO | WO 01/23583 | 4/2001 |

OTHER PUBLICATIONS

Zhu et al., "The use of exonuclease III for polymerase chain reaction sterilization," Nucleic Acids Research, 1991, vol. 19, No. 9 p. 2511.*
Nilsen et al., "Distribution of Thermophilic Marine Sulfate Reducers in North Sea Oil Field Waters and Oil Reservoirs," Applied and Environmental Microbiology, May 1996, No. 62, No. 5, pp. 1793-1798.*
Klenk et al., "The complete genome sequence of the hyperthermophilic, sulphate-reducing archaeon *Archaeoglobus fulgidus*," 1997, vol. 390, pp. 364-370.*
Ayoub Rashtchian, et al., "Uracil DNA Glycosylase-Mediated Cloning of Polymerase Chain Reaction-Amplified DNA: Application to Genomic and cDNA Cloning," *Analytical Biochemistry* (1992) 206(1): 91-97.
Booth et al., "Assembly and Cloning of Coding Sequences for Neurotrophic Factors Directly From Genomic DNA Using Polymerase Chain Reaction and Uracil DNA Glycosylase," *Gene* (1994) 146(2): 303-308.
Fromenty et al., "*Escherichia coli* Exonuclease III Enhances Long PCR Amplification of Damaged DNA Templates," *Nucleic Acids Research* (2000) 28(11): e50.
Kaluz, et al., "Directional Cloning of PCR Products Using Exonuclease III," *Nucleic Acids Research* (1992) 20(16): 4369-4370.

(Continued)

*Primary Examiner*—Kenneth R. Horlick
*Assistant Examiner*—Young J. Kim
(74) *Attorney, Agent, or Firm*—Townsend & Townsend & Crew LLP

(57) ABSTRACT

A purified thermostable enzyme is derived from the thermophilic archaebacterium *Archaeoglobus fulgidus*. The enzyme can be native or recombinant, is stable under PCR conditions and exhibits double strand specific exonuclease activity. It is a 3'–5' exonuclease and cleaves to produce 5'-mononucleotides. Thermostable exonucleases are useful in many recombinant DNA techniques, in combination with a thermostable DNA polymerase like Taq especially for nucleic acid amplification by the polymerase chain reaction (PCR).

4 Claims, 16 Drawing Sheets

OTHER PUBLICATIONS

Accession No. NC_000917 Klenk, et al., "*Archaeoglobus fulgidus* Section 43 of 172 of the Complete Genome," *EMBL Sequence Database* (1997).

Klenk, et al., "The Complete Genome Sequence of the Hyperthermophilic, Sulphate-Reducing Archaeon *Archaeoglobus fulgidus,*" *Nature* (1997) 390: 364-370.

Accession No. AE001064, TrEMBLrel 029675 (1998); Exodeoxyribonuclease III (XTHA).

Smith, et al., "Generation of Cohesive Ends on PCR Products by UDG-Mediated Excision of FU, and Application for Cloning Into Restriction Digest-Linearized Vectors," *PCR Methods and Applications* (1993) 2(4): 328-332.

* cited by examiner

Figure 1:

Nucleotide sequence (SEQ ID NO: 17) and corresponding amino acid sequence (SEQ ID NO: 18) of the *Archaeoglobus fulgidus* exonuclease III gene:

```
atg ctc aaa atc gcc acc ttc aac gta aac tcc atc agg agc aga ctg      48
Met Leu Lys Ile Ala Thr Phe Asn Val Asn Ser Ile Arg Ser Arg Leu
1               5                   10                  15 cac atc gtg att ccg tgg ctg aag gag aac aag cct gac att cta tgc      96
His Ile Val Ile Pro Trp Leu Lys Glu Asn Lys Pro Asp Ile Leu Cys
                20                  25                  30 atg cag gag acg aag gtt gag aac agg aag ttt cct gag gcc gat ttt     144
Met Gln Glu Thr Lys Val Glu Asn Arg Lys Phe Pro Glu Ala Asp Phe
        35                  40                  45 cac cgc atc ggc tac cac gtc gtc ttc agc ggg agc aag gga agg aat     192
His Arg Ile Gly Tyr His Val Val Phe Ser Gly Ser Lys Gly Arg Asn
    50                  55                  60 gga gtg gcc ata gct tcc ctc gaa gag cct gag gat gtc agc ttc ggt     240
Gly Val Ala Ile Ala Ser Leu Glu Glu Pro Glu Asp Val Ser Phe Gly
65                  70                  75                  80 ctc gat tca gag ccg aag gac gag gac agg ctg ata agg gca aag ata     288
Leu Asp Ser Glu Pro Lys Asp Glu Asp Arg Leu Ile Arg Ala Lys Ile
                85                  90                  95 gct ggc ata gac gtg att aac acc tac gtt cct cag gga ttc aaa att     336
Ala Gly Ile Asp Val Ile Asn Thr Tyr Val Pro Gln Gly Phe Lys Ile
                100                 105                 110 gac agc gag aag tac cag tac aag ctc cag tgg ctt gag agg ctt tac     384
Asp Ser Glu Lys Tyr Gln Tyr Lys Leu Gln Trp Leu Glu Arg Leu Tyr
        115                 120                 125 cat tac ctt caa aaa acc gtt gac ttc aga agc ttt gct gtt tgg tgt     432
His Tyr Leu Gln Lys Thr Val Asp Phe Arg Ser Phe Ala Val Trp Cys
    130                 135                 140 gga gac atg aac gtt gct cct gag cca atc gac gtt cac tcc cca gac     480
Gly Asp Met Asn Val Ala Pro Glu Pro Ile Asp Val His Ser Pro Asp
145                 150                 155                 160 aag ctg aag aac cac gtc tgc ttc cac gag gat gcg aga agg gca tac     528
Lys Leu Lys Asn His Val Cys Phe His Glu Asp Ala Arg Arg Ala Tyr
                165                 170                 175 aaa aaa ata ctc gaa ctc ggc ttt gtt gac gtg ctg aga aaa ata cat     576
Lys Lys Ile Leu Glu Leu Gly Phe Val Asp Val Leu Arg Lys Ile His
                180                 185                 190 ccc aac gag aga att tac acc ttc tac gac tac agg gtt aag gga gcc     624
Pro Asn Glu Arg Ile Tyr Thr Phe Tyr Asp Tyr Arg Val Lys Gly Ala
        195                 200                 205
```

```
att gag cgg ggg ctg gga tgg agg gtt gat gcc atc ctc gcc acc cca        672
Ile Glu Arg Gly Leu Gly Trp Arg Val Asp Ala Ile Leu Ala Thr Pro
    210                 215                 220 ccc ctc gcc gaa aga tgc gtg gac tgc tac gca gac atc aaa ccg agg        720
Pro Leu Ala Glu Arg Cys Val Asp Cys Tyr Ala Asp Ile Lys Pro Arg
225                 230                 235                 240 ctg gca gaa aag cca tcc gac cac ctc cct ctc gtt gct gtg ttt gac        768
Leu Ala Glu Lys Pro Ser Asp His Leu Pro Leu Val Ala Val Phe Asp
                245                 250                 255 gtg tag                                                                774
Val
```

Figure 1: 1/2

Sequence of the *Archaeoglobus fulgidus* exonuclease III gene:

SEQ ID NO.: 20/21

```
        ATGCTCAAAATCGCCACCTTCAACGTAAACTCCATCAGGAGCAGACTGCACATCGTGATT
   1    ------------+----------+----------+----------+----------+----------+  60
        TACGAGTTTTAGCGGTGGAAGTTGCATTTGAGGTAGTCCTCGTCTGACGTGTAGCACTAA a       M  L  K  I  A  T  F  N  V  N  S  I  R  S  R  L  H  I  V  I  -

CCGTGGCTGAAGGAGAACAAGCCTGACATTCTATGCATGCAGGAGACGAAGGTTGAGAAC
   61   ------------+----------+----------+----------+----------+----------+  120
        GGCACCGACTTCCTCTTGTTCGGACTGTAAGATACGTACGTCCTCTGCTTCCAACTCTTG a       P  W  L  K  E  N  K  P  D  I  L  C  M  Q  E  T  K  V  E  N  -

AGGAAGTTTCCTGAGGCCGATTTTCACCGCATCGGCTACCACGTCGTCTTCAGCGGGAGC
  121   ------------+----------+----------+----------+----------+----------+  180
        TCCTTCAAAGGACTCCGGCTAAAAGTGGCGTAGCCGATGGTGCAGCAGAAGTCGCCCTCG a       R  K  F  P  E  A  D  F  H  R  I  G  Y  H  V  V  F  S  G  S  -

AAGGGAAGGAATGGAGTGGCCATAGCTTCCCTCGAAGAGCCTGAGGATGTCAGCTTCGGT
  181   ------------+----------+----------+----------+----------+----------+  240
        TTCCCTTCCTTACCTCACCGGTATCGAAGGGAGCTTCTCGGACTCCTACAGTCGAAGCCA a       K  G  R  N  G  V  A  I  A  S  L  E  E  P  E  D  V  S  F  G  -

CTCGATTCAGAGCCGAAGGACGAGGACAGGCTGATAAGGGCAAAGATAGCTGGCATAGAC
  241   ------------+----------+----------+----------+----------+----------+  300
        GAGCTAAGTCTCGGCTTCCTGCTCCTGTCCGACTATTCCCGTTTCTATCGACCGTATCTG a       L  D  S  E  P  K  D  E  D  R  L  I  R  A  K  I  A  G  I  D  -

GTGATTAACACCTACGTTCCTCAGGGATTCAAAATTGACAGCGAGAAGTACCAGTACAAG
  301   ------------+----------+----------+----------+----------+----------+  360
        CACTAATTGTGGATGCAAGGAGTCCCTAAGTTTTAACTGTCGCTCTTCATGGTCATGTTC a       V  I  N  T  Y  V  P  Q  G  F  K  I  D  S  E  K  Y  Q  Y  K  -

CTCCAGTGGCTTGAGAGGCTTTACCATTACCTTCAAAAAACCGTTGACTTCAGAAGCTTT
  361   ------------+----------+----------+----------+----------+----------+  420
        GAGGTCACCGAACTCTCCGAAATGGTAATGGAAGTTTTTTGGCAACTGAAGTCTTCGAAA a       L  Q  W  L  E  R  L  Y  H  Y  L  Q  K  T  V  D  F  R  S  F  -

GCTGTTTGGTGTGGAGACATGAACGTTGCTCCTGAGCCAATCGACGTTCACTCCCCAGAC
  421   ------------+----------+----------+----------+----------+----------+  480
        CGACAAACCACACCTCTGTACTTGCAACGAGGACTCGGTTAGCTGCAAGTGAGGGGTCTG a       A  V  W  C  G  D  M  N  V  A  P  E  P  I  D  V  H  S  P  D  -

AAGCTGAAGAACCACGTCTGCTTCCACGAGGATGCGAGAAGGGCATACAAAAAAATACTC
  481   ------------+----------+----------+----------+----------+----------+  540
        TTCGACTTCTTGGTGCAGACGAAGGTGCTCCTACGCTCTTCCCGTATGTTTTTTTATGAG a       K  L  K  N  H  V  C  F  H  E  D  A  R  R  A  Y  K  K  I  L  -
```

Figure 1: 2/2

```
         GAACTCGGCTTTGTTGACGTGCTGAGAAAAATACATCCCAACGAGAGAATTTACACCTTC
   541   ---------+---------+---------+---------+---------+---------+  600
         CTTGAGCCGAAACAACTGCACGACTCTTTTTATGTAGGGTTGCTCTCTTAAATGTGGAAG a          E  L  G  F  V  D  V  L  R  K  I  H  P  N  E  R  I  Y  T  F   -

TACGACTACAGGGTTAAGGGAGCCATTGAGCGGGGGCTGGGATGGAGGGTTGATGCCATC
   601   ---------+---------+---------+---------+---------+---------+  660
         ATGCTGATGTCCCAATTCCCTCGGTAACTCGCCCCCGACCCTACCTCCCAACTACGGTAG a          Y  D  Y  R  V  K  G  A  I  E  R  G  L  G  W  R  V  D  A  I   -

CTCGCCACCCCACCCCTCGCCGAAAGATGCGTGGACTGCTACGCAGACATCAAACCGAGG
   661   ---------+---------+---------+---------+---------+---------+  720
         GAGCGGTGGGGTGGGGAGCGGCTTTCTACGCACCTGACGATGCGTCTGTAGTTTGGCTCC a          L  A  T  P  P  L  A  E  R  C  V  D  C  Y  A  D  I  K  P  R   -

CTGGCAGAAAAGCCATCCGACCACCTCCCTCTCGTTGCTGTGTTTGACGTGTAG
   721   ---------+---------+---------+---------+---------+----  774
         GACCGTCTTTTCGGTAGGCTGGTGGAGGGAGAGCAACGACACAAACTGCACATC a          L  A  E  K  P  S  D  H  L  P  L  V  A  V  F  D  V  *    -
```

Temperature stability of *Afu* exonuclease III

Test for exonuclease III activity 1 2 3 4 5 6 7 8 9 10 11 12 13 14

Principle of the 3'-primer correction assay

Mismatched primer correction in PCR

Figure 6A

Error rates of different DNA polymerases in PCR

| Polymerase | Template conc. (ng) | yield (ng) | DNA duplications d | blue colonies lacI⁻ | white colonies lac⁺ | total number of colonies | % lac⁻ | error rate ($f_{349}$) |
|---|---|---|---|---|---|---|---|---|
| Taq Ch. | 10 | 11650 | 10.2 | 130 | 2261 | 2391 | 5.4 | $1.57 \times 10^{-5}$ |
| HiFi Ch. | 10 | 11550 | 10.2 | 40 | 5458 | 5498 | 0.72 | $2.06 \times 10^{-6}$ |
| Pwo | 10 | 9675 | 9.9 | 17 | 5891 | 5908 | 0.29 | $8.32 \times 10^{-7}$ |
| Taq/Exo 1 | 10 | 11550 | 10.2 | 94 | 4291 | 4385 | 2.14 | $6.10 \times 10^{-6}$ |
| Taq/Exo 2 | 10 | 11125 | 10.1 | 146 | 7644 | 7790 | 1.87 | $5.36 \times 10^{-6}$ |
| Taq/Exo 3 | 10 | 8500 | 9.7 | 133 | 8188 | 8321 | 1.6 | $4.74 \times 10^{-6}$ |
| Taq/Exo 4 | 10 | 1292 | 7 | 79 | 7236 | 7315 | 1.08 | $4.44 \times 10^{-6}$ |
| Taq/Exo 5 | 10 | 236 | 4.6 | 25 | 2674 | 2724 | 0.92 | $1.16 \times 10^{-5}$ (*) |

\* Due to the unfavorable ratio of Taq:Exo the product yield was low. This results in an apparently low amplification efficiency d, which is an important parameter in the formula used for the calculation of the error rate.

UNG treatment of dUMP containing PCR products

THERMOSTABLE ENZYME PROMOTING THE FIDELITY OF THERMOSTABLE DNA POLYMERASES-FOR IMPROVEMENT OF NUCLEIC ACID SYNTHESIS AND AMPLIFICATION IN VITRO

The present invention is related to the field of molecular biology, and more particular, to poly-nucleotide synthesis. The present invention also relates to a substantially pure thermostable exo-nuclease, the cloning and expression of a thermostable exonuclease III in *E. coli*, and its use in amplification reactions. The invention facilitates the high fidelity amplification of DNA under conditions which allow decontamination from carry over and the synthesis of long products. The invention may be used for a variety of industrial, medical and forensic purposes.

In vitro nucleic acid synthesis is routinely performed with DNA polymerases with or without additional polypeptides. DNA polymerases are a family of enzymes involved in DNA replication and repair. Extensive research has been conducted on the isolation of DNA polymerases from mesophilic microorganisms such as *E. coli*. See, for example, Bessman et al. (1957) *J. Biol. Chem.* 223:171–177, and Buttin and Kornberg, (1966) *J. Biol. Chem.* 241:5419–5427.

Research has also been conducted on the isolation and purification of DNA polymerases from thermophiles, such as *Thermus aquaticus* Chien, A. et al., (1976) *J. Bacteriol.* 127:1550–1557 discloses the isolation and purification of a DNA polymerase with a temperature optimum of 80° C. from *Thermus aquaticus* YT1 strain. U.S. Pat. No. 4,889, 818 discloses a purified thermostable DNA polymerase from *T. aquaticus*, Taq polymerase, having a molecular weight of about 86,000 to 90,000 daltons. In addition, European Patent Application 0 258 017 discloses Taq polymerase as the preferred enzyme for use in the PCR process.

Research has indicated that while Taq DNA polymerase has a 5'–3' polymerase-dependent exo-nuclease function, Taq DNA polymerase does not possess a 3'–5' exonuclease III function (Lawyer, F. C. et al., (1989) *J. Biol. Chem.*, 264:6427–6437; Bernad A., et al. (1989) *Cell* 59:219). The 3'–5' exonuclease activity of DNA polymerases is commonly referred to as "proofreading activity". The 3'–5' exonuclease activity removes bases which are mismatched at the 3' end of a primer-template duplex. The presence of 3'–5' exonuclease activity may be advantageous as it leads to an increase in fidelity of replication of nucleic acid strands and to the elongation of prematurely terminated products. As Taq DNA polymerase is not able to remove mismatched primer ends it is prone to base incorporation errors, making its use in certain applications undesirable. For example, attempting to clone an amplified gene is problematic since any one copy of the gene may contain an error due to a random misincorporation event. Depending on the cycle in which that error occurs (e.g., in an early replication cycle), the entire DNA amplified could contain the erroneously incorporated base, thus, giving rise to a mutated gene product.

There are several thermostable DNA polymerases known in the art which exhibit 3'–5' exonuclease activity, like B-type polymerases from thermophilic Archaebacteria which are used for high fidelity DNA amplification. Thermostable polymerases exhibiting 3'–5' exonuclease activity may be isolated or cloned from *Pyrococcus* (Purified thermostable *Pyrococcus furiosus* DNA polymerase, Mathur E., Stratagene, WO 92/09689, U.S. Pat. No. 5,545,552; Purified thermostable DNA polymerase from *Pyrococcus* species, Comb D. G. et al., New England Biolabs, Inc., EP 0 547 359; Organization and nucleotide sequence of the DNA polymerase gene from the archaeon *Pyrococcus furiosus*, Uemori T. et al. (1993) *Nucl. Acids Res.,* 21:259–265.), from *Pyrodictium* spec. (Thermostable nucleic acid polymerase, Gelfand D. H., F. Hoffmann-La Roche A G, EP 0 624 641; Purified thermostable nucleic acid polymerase and DNA coding sequences from *Pyrodictium* species, Gelfand D. H., Hoffmann-La Roche Inc., U.S. Pat. No. 5,491,086), from *Thermococcus* (e.g. Thermostable DNA polymerase from *Thermococcus* spec. T Y, Niehaus F., et al. WO 97/35988; Purified *Thermocccus barossii* DNA polymerase, Luhm R. A., Pharmacia Biotech, Inc., WO 96/22389; DNA polymerase from *Thermococcus barossii* with intermediate exonuclease activity and better long term stability at high temperature, useful for DNA sequencing, PCR etc., Dhennezel O. B., Pharmacia Biotech Inc., WO 96/22389; A purified thermostable DNA polymerase from *Thermococcus litoralis* for use in DNA manipulations, Comb D. G., New England Biolabs, Inc., U.S. Pat. No. 5,322,785, EP 0 455 430; Recombinant thermostable DNA polymerase from Archaebacteria, Comb D. G., New England Biolabs, Inc., U.S. Pat. No. 5,352,778, EP 0 547 920, EP 0 701 000; New isolated thermostable DNA polymerase obtained from *Thermococcus gorgonarius*, Angerer B. et al. Boehringer Mannheim GmbH, WO 98/14590.

Another possibility of conferring PCR in the presence of a proofreading function is the use of a mixture of polymerase enzymes, one polymerase exhibiting such a proofreading activity. (e.g. Thermostable DNA polymerase with enhanced thermostability and enhanced length and efficiency of primer extension, Barnes W. M., U.S. Pat. No. 5,436,149, EP 0 693 078; Novel polymerase compositions and uses thereof, Sorge J. A., Stratagene, WO 95/16028). It is common practice to use a formulation of a thermostable DNA polymerase comprising a majority component of at least one thermostable DNA polymerase which lacks 3'–5' exonuclease activity and a minority component exhibiting 3'–5' exonuclease activity e.g. Taq polymerase and Pfu DNA polymerase. In these mixtures the processivity is conferred by the pol I-type enzyme like Taq polymerase, the proofreading function by the thermostable B-type polymerase like Pfu. High fidelity DNA synthesis is one desirable parameter in nucleic acid amplification, another important feature is the possibility of decontamination.

The polymerase chain reaction can amplify a single molecule over a billionfold. Thus, even minuscule amounts of a contaminant can be amplified and lead to a false positive result. Such contaminants are often poducts from previous PCR amplifications (carry-over contamination). Therefore, researchers have developed methods to avoid such a contamination.

The procedure relies on substituting dUTP for TTP during PCR amplification to produce uracil-containing DNA (U-DNA). Treating subsequent PCR reaction mixtures with Uracil-DNA-Gly-cosylase (UNG) prior to PCR amplification the contaminating nucleic acid is degraded and not suitable for amplification. dUTP can be readily incorporated by polI-type thermostable polymerases but not B-type polymerases (G. Slupphaug, et al. (1993) *Anal. Biochem.* 211: 164–169) Low incorporation of dUTP by B-type polymerases limits their use in laboratories where the same type of template is repeatedly analyzed by PCR amplification.

Thermostable DNA polymerases exhibiting 3'–5' exonuclease activity were also isolated from eubacterial strains like *Thermotoga* (Thermophilic DNA polymerases from *Thermotoga neapolitana*, Slater M. R. et al. Promega Corporation, WO 96/41014; Cloned DNA polymerases from

*Thermotoga neapolitana* and mutants thereof, Hughes A. J. et al., Life Technologies, Inc. WO 96/10640; Purified thermostable nucleic acid polymerase enzyme from *Termotoga maritima*, Gelfand D. H. et al., CETUS Corporation, WO 92/03556) These enzymes have a strong 3'–5' exo-nuclease activity which is able to eliminate misincorporated or mismatched bases. A genetically engineered version of this enzyme is commercially available as ULTma, a DNA polymerase which can be used without additional polypeptides for the PCR process. This enzyme is able to remove misincorporated bases, incorporate dUTP, but the fidelity is for unknown reasons not higher than that of Taq polymerase (Accuracy of replication in the polymerase chain reaction. Diaz R. S. et al. *Braz. J. Med. Biol. Res.* (1998) 31: 1239–1242; PCR fidelity of Pfu DNA polymerase and other thermostable DNA polymerases, Cline J. et al., *Nucleic Acids Res.* (1996) 24:3546–3551).

For high fidelity DNA synthesis another alternative to the use of B-type polymerases or mixtures containing them is the use of thermophilic DNA polymerase III holoenzyme, a complex of 18 polypeptide chains. These complexes are identical to the bacterial chromosomal replicases, comprising all the factors necessary to synthesize a DNA strand of several hundred kilobases or whole chromosomes. The 10 different subunits of this enzyme, some of which are present in multiple copies, can be produced by recombinant techniques, reconstituted and used for in vitro DNA synthesis. As a possible use of these complexes PCR amplification of nucleic acis of several thousand to hundreds of thousand base pairs is proposed. (Enzyme derived from thermophilic organisms that functions as a chromosomal replicase, and preparation and uses thereof, Yurieva O. et al., The Rockefeller University, WO 98/45452; Novel thermophilic polymerase III holoenzyme, McHenry C., ENZYCO Inc., WO 99/13060)

It was aimed according to this invention to develop a high fidelity PCR system which is preferably concomitantly able to incorporate dUTP. According to the present invention a thermostable enzyme exhibiting 3'-exonuclease-activity but essentially no DNA polymerase activity is provided whereas this enzyme enhances fidelity of an amplification process when added to a second enzyme exhibiting polymerase activity. The enzyme provided can excise mismatched primer ends to allow the second enzyme exhibiting polymerase activity as e.g. Taq polymerase to reassociate and to reassume elongation during a process of synthezising DNA. The inventive enzyme is able to cooperate as proofreading enzyme with a second enzyme exhibiting polymerase activity. The enzyme that was found to be suitable for this task is e.g. a thermostable exonuclease III. Preferred is an exonuclease III working from the 3' to 5' direction, cleaving 5' of the phosphate leaving 3' hydroxyl groups and ideally working on double stranded DNA only. The 3'–5'exonuclease functions of DNA polymerases are active on double and single stranded DNA. The latter activity may lead to primer degradation, which is undesired in PCR assays. It is preferred that the enzyme is active at 70° C. to 80° C., stable enough to survive the denaturation cycles and inactive at lower temperatures to leave the PCR products undegraded after completion of the PCR process. Enzymes exhibiting these features can be derived from thermophilic eubacteria or related enzymes from thermophilic archaea. Genomes of three thermostable archaebacteria are sequenced, *Methanococcus jannaschii* (Complete Genome Sequence of the Methanogenic Archaeon, *Methanococcus jannaschii*, Bult C. J. et al., (1996) *Science* 273: 1058–1072), *Methanobacterium thermoautotrophicum* (Complete genomic sequence of *Methanobacterium thermoautotrophicum* ΔH: Functional Analysis and Comparative Genomics, Smith D. R. et al., *J. of Bacteriology* (1997) 179: 7135–7155) and *Archaeoglobus fulgidus* (The complete genome sequence of the hyperthermophilic, sulfate-reducing archaeon *Archaeoglobus filgidus*, Klenk H.-P. et al. (1997) *Nature* 390: 364–370).

In particular, there is provided a thermostable enzyme obtainable from *Archaeoglobus fulgidus*, which catalyzes the degradation of mismatched ends of primers or polynucleotides in the 3' to 5' direction in double stranded DNA. The gene encoding the thermostable exonuclease III obtainable from *Archaeoglobus fulgidus* (Afu) was cloned, expressed in *E. coli* and isolated. The enzyme is active under the incubation and temperature conditions used in PCR reactions. The enzyme supports DNA polymerases like Taq in performing DNA synthesis at low error rates and synthesis of products of more than 3 kb on genomic DNA—the upper range of products synthesized by Taq polymerase—in good yields with or without dUTP present in the reaction mixture. Preferably, 50–500 ng of the exonuclease III obtainable from Afu were used per 2,5 U of Taq polymerase in order to have an optimal PCR performance. More preferably is the use of 67 ng to 380 ng of the exonuclease III obtainable from Afu per 2,5 U of the Taq polymerase in the PCR reaction.

Thus, the inventive enzyme is able to cooperate as proofreading enzyme with Taq polymerase. The advantage of the use of the inventive enzyme in comparison to other enzymes is that the inventive enzyme is preferably active on double stranded DNA. The thermostable enzyme of this invention may be used for any purpose in which such enzyme activity is necessary or desired. In a particularly preferred embodiment the enzyme is used in combination with a thermostable DNA polymerase in the nucleic acid amplification reaction known as PCR in order to remove mismatched primer ends which lead to premature stops, to provide primer ends which are more effectively elongated by the polymerase, to correct for base incorporation errors and to enable the polymerase to produce long PCR products.

Further, subject of the present invention is a composition comprising a first thermostable enzyme exhibiting 3'-exonuclease-activity but essentially no DNA polymerase activity and a second enzyme exhibiting polymerase activity whereas the fidelity of an amplification process is enhanced by the use of this composition in comparison to the use of the second enzyme alone. The inventive thermostable enzyme exhibiting 3'-exonuclease-activity but essentially no DNA polymerase activity also includes appropriate enzymes exhibiting reduced DNA polymerase activity or no such activity at all. Reduced DNA polymerase activity according to the invention means less than 50% of said activity of an enzyme exhibiting DNA polymerase activity. In a preferred embodiment the second enzyme of the inventive composition is lacking proofreading activity. In particular preferred, the second enzyme is Taq polymerase.

A further subject of the present invention is a method of synthesis using a mixture comprising a first thermostable enzyme exhibiting 3'-exonuclease-activity but essentially no DNA polymerase activity and a second enzyme exhibiting polymerase activity. According to this method prematurely terminated chains are trimmed by degradation from 3' to 5'. Mismatched ends of either a primer or the growing strand are removed according to this method.

The invention further comprises a method according to the above description whereas dUTP is present in the reaction mixture, replacing partly or completely TTP. It is preferred that according to this method uracil DNA glycosylase (UDG or UNG) is used for degradation of contaminating nucleic acids.

Preferably, according to this method the mixture of a
  a first thermostable enzyme exhibiting 3'-exonuclease-activity but essentially no DNA polymerase activity and
  a second enzyme exhibiting poly erase activity produces PCR products with lower error rates compared to PCR products produced by the second enzyme exhibiting polymerase activity in absence of the first thermostable enzyme exhibiting 3'-exonuclease-activity but essentially no DNA polymerase activity. The method in which the mixture of first thermostable enzyme exhibiting 3'-exonuclease-activity but essentially no DNA polymerase activity and a second enzyme exhibiting polymerase activity produces PCR products of greater length compared to PCR products produced by the second enzyme exhibiting polymerase activity in absence of the first thermostable enzyme exhibiting 3'-exonuclease-activity but essentially no DNA polymerase activity. Further, the first thermostable enzyme exhibiting 3'-exonuclease-activity but essentially no DNA polymerase activity is related to the Exonuclease III of *E. coli*, but thermostable according to this method. A further embodiment of the above described method is the method whereas PCR products with blunt ends are obtained.

Subject of the present invention are also methods for obtaining the inventive thermostable enzyme exhibiting 3' exonuclease-activity but essentially no DNA polymerase activity and means and materials for producing this enzyme as e.g. vectors and host cells (e.g. DSM no. 13021).

The following examples are offered for the purpose of illustrating, not limiting, the subject invention.

BRIEF DESCRIPTION OF THE DRAWINGS

FIG. 1:
DNA sequence (SEQ ID NO: 17) and the deduced amino acid sequence (SEQ ID NO: 18) of the gene encoding the DNA polymerase from exonuclease III *Archaeoglobus fulgidis*.

Figure 2:
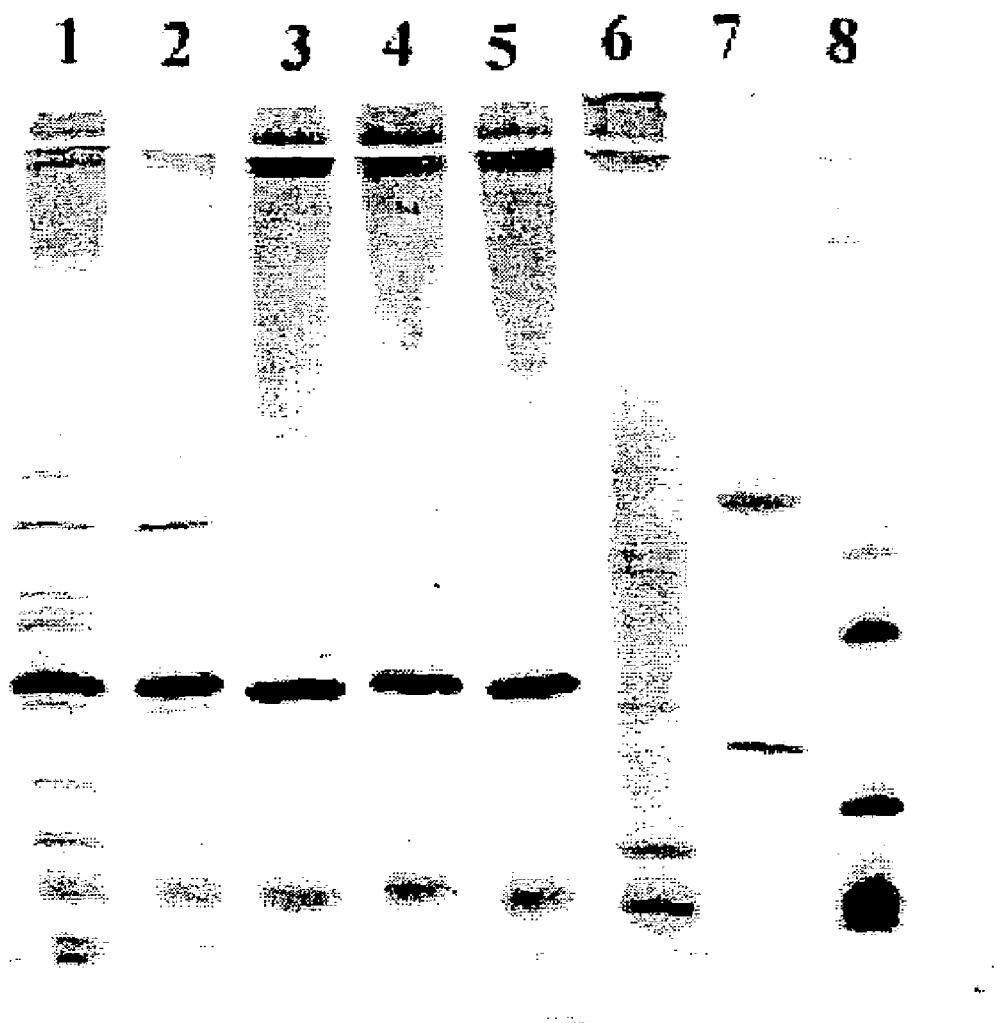
FIG. 2:
Resistance to heat denaturation of the recombinant exonuclease III of *Archaeoglobus fulgidus* expressed in *E. coli* as described in Example V.
  Lane 1: Incubation at 50° C.
  Lane 2: Incubation at 60° C.
  Lane 3: Incubation at 70° C.
  Lane 4: Incubation at 80° C.
  Lane 5: Incubation at 90° C.
  Lane 6: *E. coli* host cell extract not transformed with gene encoding Afu exonuclease III
  Lane 7: Exonuclease III of *E. coli*
  Lane 8: Molecular weight marker

Error rates of different polymerases in PCR

FIG. 6B:

Improvement of fidelity by Afu exonuclease III present in the PCR mixture as described in Example VIII.

The ratio of blue:white colonies were blottet and various mixtures of Taq DNA polymerase and Afu exonuclease III (Taq/Exo 1:30, Taq/Exo 1:20, Taq/Exo 1:15, Taq/Exo 1:12, 5, Taq/Exo 1:10 corresponding to 2.5 units of Taq DNA polymerase mixed with 125 ng, 175 ng, 250 ng, 375 ng and 500 ng of Afu exonuclease III, respectively) were tested in comparison to Taq DNA polymerase (Taq), Expand HiFi PCR System (HiFi) and Pwo DNA polymerase (Pwo).

FIG. 7:

Incorporation of dUTP by the Taq DNA polymerase/Afu exonuclease III mixture as described in Example IX Lane 1: DNA Molecular Weight Marker XIV (Roche Molecular Biochemicals No. 1721933)

Lane 2: Amplification with 2.5 units Taq DNA polymerase

Lane 3: Amplification with 2.5 units Taq DNA polymerase and 125 ng of Afu exonuclease III Lane 4: Amplification with 2.5 units Taq DNA polymerase and 250 ng of Afu exonuclease III Lane 5: Amplification with 2.5 units Taq DNA polymerase and 375 ng of Afu exonuclease III Lane 6: Amplification with 2.5 units Taq DNA polymerase and 500 ng of Afu exonuclease III

FIG. 8:

Degradation of dUTP containing PCR products by Uracil-DNA Glycosylase as described in Example IX.

Lane 1: DNA Molecular Weight Marker XIV (Roche Molecular Biochemicals No. 1721933)

Lane 2: 1 µl of the amplification product obtained with Taq DNA polymerase and 125 ng of Afu exonuclease III and subsequent UNG and heat treatment.

Lane 3: 2 µl of the amplification product obtained with Taq DNA polymerase and 125 ng of Afu exonuclease III and subsequent UNG and heat treatment.

Lane 4: 3 µl of the amplification product obtained with Taq DNA polymerase and 125 ng of Afu exonuclease III and subsequent UNG and heat treatment.

Lane 5: 4 µl of the amplification product obtained with Taq DNA polymerase and 125 ng of Afu exonuclease III and subsequent UNG and heat treatment.

Lane 6: 5 µl of the amplification product obtained with Taq DNA polymerase and 125 ng of Afu exonuclease III and subsequent UNG and heat treatment.

Lane 7: 5 µl of the amplification product obtained with Taq DNA polymerase and 125 ng of Afu exonuclease III no subsequent UNG or heat treatment.

Lane 8: 5 µl of the amplification product obtained with Taq DNA polymerase and 125 ng of Afu exonuclease III no subsequent UNG but heat treatment.

Lane 9: DNA Molecular Weight Marker XIV (Roche Molecular Biochemicals No. 1721933)

FIG. 9:

Effect of Afu exonuclease III on PCR product length. The Taq DNA polymerase/Afu exonuclease III mixture was analyzed on human genomic DNA as described in Example X.

Lane 1: 9,3 kb tPA fragment with Taq/Exo III Mix

Lane 2: ,, Taq-Pol.

Lane 3: 12 kb tPA fragment with Taq/Exo III Mix

Lane 4: ,, Taq-Pol.

Lane 5: 15 kb tPA fragment with Taq/Exo III Mix

Lane 6: ,, Taq-Pol.

FIG. 10:

Thermostable exonuclease III can be replaced by a polymerase mutant with reduced polymerase activity but increased 3'-exonucleoase-activity as described in Example XI.

Lane 1: Molecular Weight Marker

Lane 2: reaction 1, Taq polymerase, 4.8 kb fragment

Lane 3: reaction 2, Taq polymerase plus Tag polymerase mutant, 4.8 kb fragment

Lane 4: reaction 3, no Taq polymerase, Tag polymerase mutant, 4.8 kb fragment

Lane 5: reaction 4, Taq polymerase plus Afu ExoIII, 4.8 kb fragment

Lane 6: reaction 5, Taq polymerase, 9.3 kb fragment

Lane 7: reaction 6, Taq polymerase plus Tag polymerase mutant, 9.3 kb fragment Lane 8: reaction 7, no Taq polymerase, Tag polymerase mutant, 9.3 kb fragment Lane 9: reaction 8, Taq polymerase plus Afu ExoIII, 9.3 kb fragment Lane 10: Molecular Weight Marker

FIG. 11.

Afu exonuclease III is not active on linear single stranded DNA as described in Example XII Lane 1: Afu Exo III, no incubation Lane 2: Afu Exo III, 1 h at 65° C.

Lane 3: Afu Exo III, 2 h at 65° C.

Lane 4: Afu Exo III, 3 h at 65° C.

Lane 5: Afu Exo III, 4 h at 65° C.

Lane 6: Afu Exo III, 5 h at 65° C.

Lane 7: Reaction buffer without enzyme, no incubation

Lane 8: Reaction buffer without enzyme, 5 h at 65° C.

Lane 9: Molecular Weight Marker

FIG. 12:

Comparison of Afu exonuclease III with a thermostable B-type polymerase in primer degradating activity as described in Example XIII.
Lane 1: Molecular Weight Marker
Lane 2: 1 u Tgo preincubated (reaction 1)
Lane 3: 1.5 u Tgo, preincubated (reaction 2)
Lane 4: 1 u Tgo, not preincubated (reaction 3)
Lane 5: 1.5 u Tgo, not preincubated (reaction 4)
Lane 6: 1 u Tgo, preincubated in the absence of dNTPs (reaction 5)
Lane 7: 1.5 u Tgo, preincubated in the absence of dNTPs (reaction 6)
Lane 8: 1 u Tgo, not preincubated in the absence of dNTPs (reaction 7)
Lane 9: 1.5 u Tgo, not preincubated in the absence of dNTPs (reaction 8)
Lane 10: 1 u Tgo, preincubated, in the absence of dNTPs, supplemented with additional primer (reaction 9)
Lane 11: 1.5 u Tgo, preincubated in the absence of dNTPs, supplemented with additional primer (reaction 10)
Lane 12: Taq polymerase, preincubated (reaction 11)
Lane 13: Taq plus 37,5 ng Afu Exo III, preincubated (reaction 12)
Lane 14: Taq plus 75 ng Afu Exo III, preincubated (reaction 13)
Lane 15: Taq polymerase, not preincubated (reaction 14)
Lane 16: Taq plus 37,5 ng Afu Exo III, not preincubated (reaction 15)
Lane 17: Taq plus 75 ng Afu Exo III, not preincubated (reaction 16)
Lane 18: Molecular Weight Marker

DETAILED DESCRIPTION OF THE PREFERRED EMBODIMENTS

EXAMPLE I

Isolation of Coding Sequences

The preferred thermostable enzyme herein is an extremely thermostable exodeoxyribonuclease obtainable from *Archaeoglobus fulgidus* VC-16 strain (DSM No. 4304). The strain was isolated from marine hydrothermal systems at Vulcano island and Stufe di Nerone, Naples, Italy (Stetter, K. O. et al., Science (1987) 236:822–824). This organism is an extremely thermophilic, sulfur metabolizing, archaebacteria, with a growth range between 60° C. and 95° C. with optimum at 83° C. (Klenk, H. P. et al., Nature (1997) 390:364–370). The genome sequence is deposited in the TIGR data base. The gene putatively encoding exonuclease III (xthA) has Acc.No. AF0580.

The apparent molecular weight of the exodeoxyribonuclease obtainable from *Archaeoglobus fulgidus* is about 32,000 daltons when compared with protein standards of known molecular weight (SDS-PAGE). The exact molecular weight of the thermostable enzyme of the present invention may be determined from the coding sequence of the *Archaeoglobus fulgidus* exodeoxyribonuclease III gene.

EXAMPLE II

Cloning of the Gene Encoding Exonuclease Iii from *Archaeoglobus fulgidus*

About 6 ml cell culture of DSM No. 4304 were used for isolation of chromosomal DNA from *Archaeoglobus fulgidus*.

The following primers were designed with restriction sites compatible to the multiple cloning site of the desired expression vector and complementary to the N- and C-terminus of the *Archaeoglobus fulgidus* exonuclease III gene:
SEQ ID NO.: 1
N-terminus (BamHI-site): 5'-GAA ACG AGG ATC CAT GCT CAA AAT CGC CAC C-3'
SEQ ID NO.: 2
C-terminus (PstI-site): 5'-TTG TTC ACT GCA GCT ACA CGT CAA ACA CAG C-3'

First the cells were collected by repeted centrifugation in one 2 ml eppendorf cap at 5,000 rpm. The DNA isolation may be performed with any described method for isolation from bacterial cells. In this case the *Archaeoglobus fulgidus* genomic DNA was prepared with the High Pure™ PCR Template Preparation Kit (ROCHE Diagnostics GmbH, No. 1796828). With this method about 6 µg chromosomal DNA were obtained with a concentration of 72 ng/µl.

PCR was performed with the primers described above, in the Expand™ High Fidelity PCR System (ROCHE Diagnostics GmbH, No. 1732641) and 100 ng *Archaeoglobus fulgidus* genomic DNA per cap in four identical preparations. PCR was performed with the following conditions:
1× 94° C., 2 min;
10× 94° C., 10 sec; 54° C., 30 sec; 68° C., 3 min;
20× 94° C., 10 sec; 54° C., 30 sec; 68° C., 3 min with 20 sec cycle elongation for each cycle;
1× 68° C., 7 min;

After adding $MgCl_2$ to a final concentration of 10 mM the PCR product was cleaved with BamHI and Pst I, 10 units each, at 37° C. for 2 hours. The reaction products were separated on a low-melting agarose gel. After elecrophoresis the appropriate bands were cut out, the gel slices combined, molten, the DNA fragments isolated by agarase digestion and precipitated with EtOH. The dried pellet was diluted in 30 µl $H_2O$.

The appropriate expression vector, here pDS56_T, was digested with the same restriction enzymes as used for the insert and cleaned with the same method.

After ligation of insert and vector with the Rapid DNA Ligation Kit (ROCHE Diagnostics GmbH, No. 1635379) the plasmid was transformed in the expression host *E. coli* 392 pUBS520 (Brinkmann, U. et al. (1989) Gene 85:109–114).

Plasmid DNA of the transformants was isolated using the High Pure™ Plasmid Isolation Kit (ROCHE Diagnostics GmbH, No.1754777) and characterized by restriction digestion with BamHI and PstI and agarose gel electrophoresis.

Positive *E. coli* pUBS520 ExoIII transformants were stored in glycerol culture at −70° C. The sequence of the gene encoding exonuclease III was confirmed by DNA sequencing. It is shown in FIG. 1.

Cloning and expression of exonuclease III from *Archaeoglobus fulgidus* or other thermophilic organisms may also be performed by other techniques using conventional skill in the art (see for example Sambrook et al. Molecular Cloning, A Laboratory Manual, Cold Spring Harbour Lab., 1989).

EXAMPLE III

Expression of Recombinant Afu Exonuclease III

The transformant from example I was cultivated in a fermentor in a rich medium containing appropriate antibiotic. Cells were harvested at an optical density of $[A_{540}]$ 5.5 by centrifugation and frozen until needed or lyzed by treatment with lysozyme to produce a crude cell extract containing the *Archaeoglobus fulgidus* exonuclease III activity.

The crude extract containing the *Archaeoglobus fulgidus* exonuclease III activity is purified by the method described in example IV, or by other purification techniques such as affinity-chromatography, ion-exchange-chromatography or hydrophobic-interaction-chromatography.

EXAMPLE IV

Purification of Recombinant Afu Exonuclease III

*E. coli* pUBS520 ExoIII (DSM No. 13021) from example I was grown in a 10 l fermentor in media containing tryptone (20 g/l), yeast extract (10 g/l), NaCl (5 g/l) and ampicillin (100 mg/l) at 37° C., induced with IPTG (0.3 mM) at midexponential growth phase and incubated an additional 4 hours. About 45 g of cells were harvested by centrifugation and stored at −70° C. 2 g of cells were thawed and suspended in 4 ml buffer A (40 mM Tris/HCl, pH 7.5; 0.1 mM EDTA; 7 mM 2-mercaptoethanol; 1 mM Pefabloc SC). The cells were lyzed under stirring by addition of 1.2 mg lysozyme for 30 minutes at 4° C. and addition of 4.56 mg sodium deoxycholate for 10 minutes at room temperature followed by 20 minutes at 0° C. The crude extract was adjusted to 750 mM KCl, heated for 15 minutes at 72° C. and centrifuged for removal of denatured protein.

A heating temperature up to 90° C. is also possible without destroying (denaturation) the *Archaeoglobus fulgidus* exonuclease III. The supernatant was dialyzed against buffer B (buffer A containig 10% glycerol) adjusted to 10 mM $MgCl_2$ and applied to a Blue Trisacryl M column (SERVA, No. 67031) with the dimension 1×7 cm and 5.5 ml bed volume, equilibrated with buffer B. The column was washed with 16.5 ml buffer B and the exonuclease protein was eluted with a 82 ml linear gradient of 0 to 3 M NaCl in buffer B. The column fractions were assayed for *Archaeoglobus fulgidus* exodeoxyribonuclease protein by electrophoresis on 10–15% SDS-PAGE gradient gels. The active fractions, 16.5 ml, were pooled, concentrated with Aquacide II (Calbiochem No. 17851) and dialyzed against the storage buffer C (10 mM Tris/HCl, pH 7.9; 10 mM 2-mercptoethanol; 0.1 mM EDTA; 50 mM KCl; 50% glycerol). After dialysis Thesit and Nonidet P40 were added to a final concentration of 0.5% each. This preparation was stored at −20° C.

The *Archaeoglobus fulgidus* exonuclease III obtained was pure to 95% as estimated by SDS gel electrophoresis. The yield was 50 mg of protein per 2.3 g cellmass (wetweight).

EXAMPLE V

Thermostability of Recombinant Exonuclease III from *Archaeoglobus fulgidus*

The thermostability of the exonuclease III from *Archaeoglobus fulgidus* cloned as described in Example II was determined by analyzing the resistance to heat denaturation. After lysis as described in Example IV 100 µl of the crude extract were centrifuged at 15,000 rpm for 10 min in an Eppendorf centrifuge. The supernatant was aliquoted into five new Eppendorf caps. The caps were incubated for 10 minutes at five different temperatures, 50° C., 60° C., 70° C., 80° C. and 90° C. After centrifugation as described above, aliquotes of the supernatants were analyzed by electrophoresis on 10–15% SDS-PAGE gradient gels. As shown in FIG. 2 the amount of *Archaeoglobus fulgidus* exonuclease III protein after incubation at 90° C. was the same as that of the samples treated at lower temperatures. The was no significant loss by heat denaturation detectable. From this result it can be concluded that the half life is more than ten minutes at 90° C.

EXAMPLE VI

Activity of Afu Exonuclease III

Exonuclease III catalyzes the stepwise removal of mononucleotides from 3′-hydroxyl termini of duplex DNA (Rogers G. S. and Weiss B. (1980) *Methods Enzymol.* 65:201–211). A limited number of nucleotides are removed during each binding event. The preferred substrate are blunt or recessed 3′-termini. The enzyme is not active on single stranded DNA, and 3′-protruding termini are more resistant to cleavage. The DNA Molecular Weight Marker VI (ROCHE Molecular Biochemicals, No.1062590) consists of BglI digested pBR328 mixed with HinfI digested pBR328. The products of the HinfI digest have 3′-recessive termini and are expected to be preferred substrates to degradation by exonuclease III, the products of BglI cleavage have 3′protruding ends with 3 bases overhangs and should be more resistant to cleavage by exonuclease III.

Figure 3:
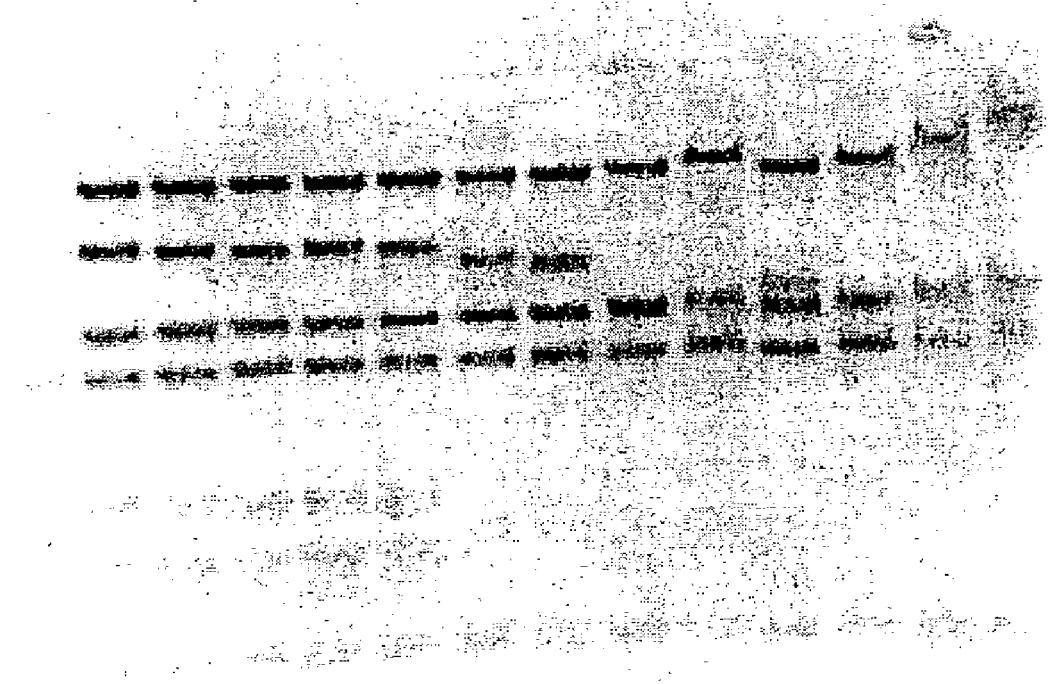
FIG. 3:
Exonuclease activity of Afu exonuclease III on DNA fragments as described in Example VI.
  Lane 1: 10 units *E. coli* exonuclease III, incubation at 37° C.
  Lane 2: 50 ng of Afu exonuclease III, incubation at 72° C.
  Lane 3: 100 ng of Afu exonuclease III, incubation at 72° C.
  Lane 4: 150 ng of Afu exonuclease III, incubation at 72° C.
  Lane 5: 100 ng of Afu exonuclease III, incubation at 72° C.
  Lane 6: 200 ng of Afu exonuclease III, incubation at 72° C.
  Lane 7: 300 ng of Afu exonuclease III, incubation at 72° C.
  Lane 8: 250 ng of Afu exonuclease III, incubation at 72° C.
  Lane 9: 750 ng of Afu exonuclease III, incubation at 72° C.
  Lane 10: 1 µg of Afu exonuclease III, incubation at 72° C.
  Lane 11: 500 ng of Afu exonuclease III, incubation at 72° C.
  Lane 12: 1 µg of Afu exonuclease III, incubation at 72° C.
  Lane 13: 1.5 µg of Afu exonuclease III, incubation at 72° C.
  Lane 14: 1.5 µg of Afu exonuclease III, incubation at 72° C.
  Lane 15: 3 µg of Afu exonuclease III, incubation at 72° C.
  Lane 16: 4.5 µg of Afu exonuclease III, incubation at 72° C.
  Lane 17: 7.6 µg of Afu exonuclease III, incubation at 72° C.
  Lane 18: 15.2 µg of Afu exonuclease III, incubation at 72° C.
  Lane 19: 22.8 µg of Afu exonuclease III, incubation at 72° C.
  Lane 20: no exonuclease added

Serial dilutions of *Archaeoglobus fulgidus* exonuclease III from Example IV were incubated for 2 hours at 72° C. with 0.5 µg DNA Molecular Weight Marker VI (ROCHE Molecular Biochemicals, No.1062590) in 25 µl of the following incubation buffer: 10 mM Tris/HCl, pH 8.0; 5 mM $MgCl_2$; 1 mM 2-mercaptoethanol; 100 mM NaCl with Paraffin overlay. 10 units of exonuclease III of *E. coli* (ROCHE Molecular Biochemicals, No.779709) was included as a control. The control reaction was performed at 37° C. After addition of 5 µl stop solution (0.2% Agarose, 60 mM EDTA, 10 mM Tris-HCl, pH 7.8, 10% Glycerol, 0.01% Bromphenolblue) the mixtures were separated on a 1% agarose gel. The result is shown in FIG. 3. Afu exonuclease III discriminates between the two different types of substrate. The preferred substrate are the fragments with 3′-recessive ends (e.g. 1766 bp fragment) and the 3′-overhanging ends (e.g. 2176 bp, 1230 bp, 1033 bp fragments) are more resistant to degradation. With higher amounts of protein the substrate is degraded to a similar extent as in lane 1, where the products of exonuclease III of *E. coli* were analyzed. With increasing amounts of Afu exonuclease protein only little DNA substrate was left (lanes 15 to 19), the retardation of the remaining fragments may be due to DNA binding proteins as impurities of the preparation.

EXAMPLE VII

Mismatched Primer Correction in PCR with Afu Exonuclease III

Figure 4:
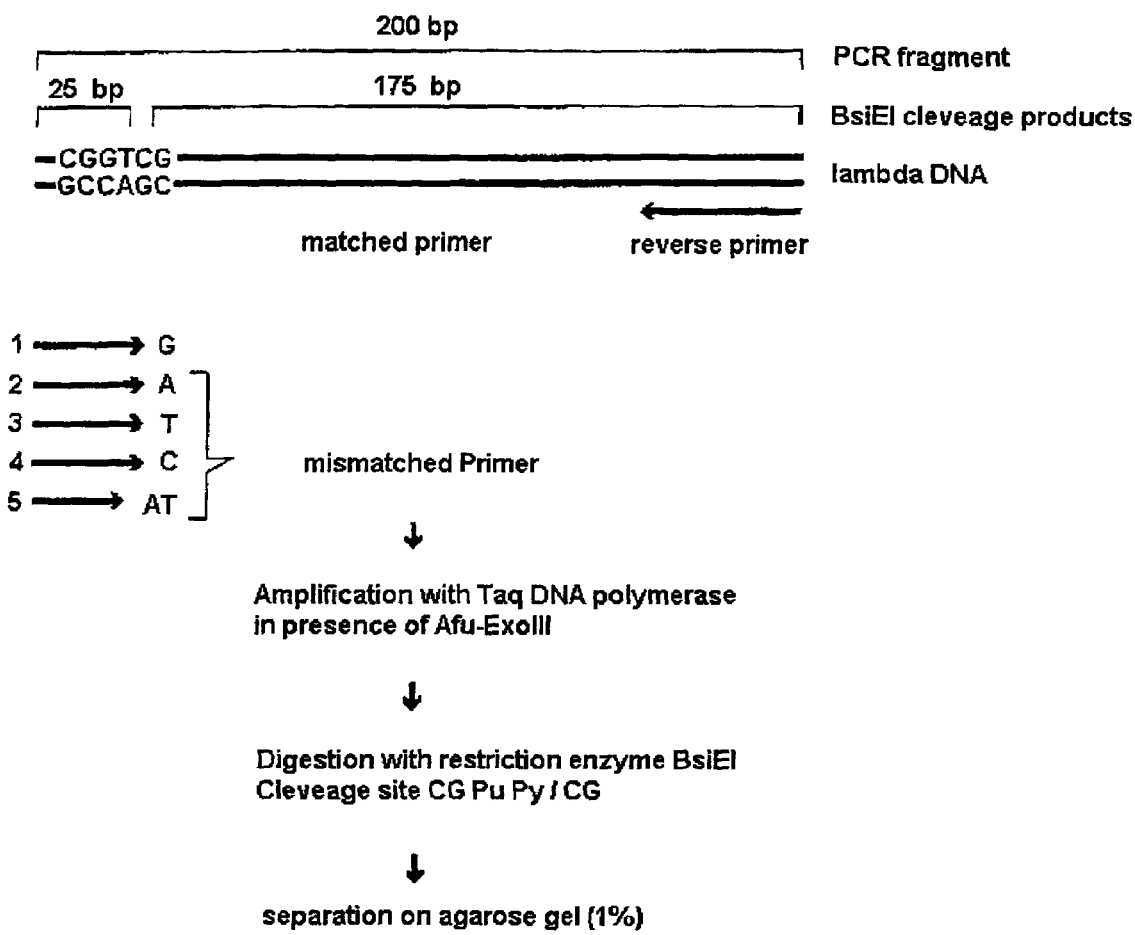
FIG. 4:
Principle of the mismatch correction assay.

The repair efficiency of the Afu exonuclease III/Taq polymerase mixture during PCR was tested with 3′ terminally mismatched primers, the principle of the assay is shown in FIG. 4. For PCR amplification sets of primers are used in which the forward primer has one or two nucleotides at the 3′ end which cannot base pair with the template DNA. Excision of the mismatched primer end and amplification of the repaired primer generates a product which can subsequently be cleaved with the restriction endonuclease BsiEI, whereas the product arising from the mismatched primer is resistant to cleavage.

The primer sequences used:
1. reverse: 5'-GGT TAT CGA AAT GAG CCA GAG CG-3' (SEQ ID NO.: 3)
2. forward 1 (g:a mismatch): 5'-TGG ATA CGT CTG AAC TGG TCA CGG TCA-3'(SEQ ID NO.: 4)
3. forward 2 (g:t mismatch): 5'-TGG ATA CGT CTG AAC TGG TCA CGG TCT-3' (SEQ ID NO.: 5)
4. forward 3 (g:c mismatch): 5'-TGG ATA CGT CTG AAC TGG TCA CGG TCC-3' (SEQ ID NO.: 6)
5. forward 4 (2 base mismatch): 5'-TGG ATA CGT CTG AAC TGG TCA CGG TAT-3' (SEQ ID NO.: 7)

Figure 5:
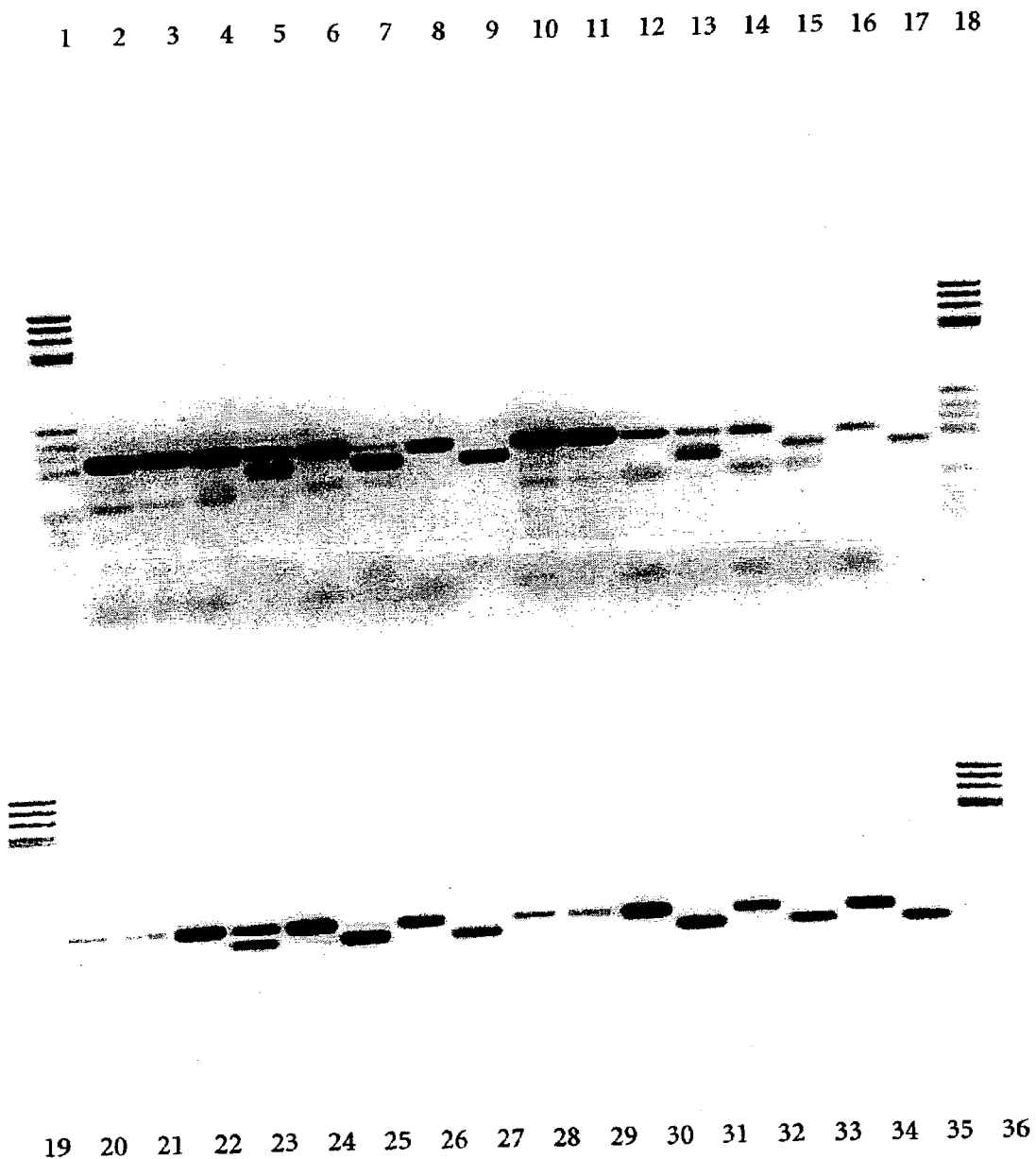
FIG. 5:
Mismatched primer correction in PCR as described in Example VII.
  Lane 1: DNA Molecular Weight Marker V (ROCHE Molecular Biochemicals No. 821705)
  Lane 2: G:A mismatched primer, amplification with Taq DNA polymerase
  Lane 3: same as in lane 2, but subsequently cleaved with BsiEI
  Lane 4: G:A mismatched primer, amplification with Expand HiFi PCR System
  Lane 5: same as in lane 4, but subsequently cleaved with BsiEI
  Lane 6: G:A mismatched primer, amplification with Taq polymerase/Afu exonuclease III
  Lane 7: same as in lane 6, but subsequently cleaved with BsiEI
  Lane 8: G:A mismatched primer, amplification with Tgo DNA polymerase
  Lane 9: same as in lane 8, but subsequently cleaved with BsiEI
  Lane 10: G:T mismatched primer, amplification with Taq DNA polymerase
  Lane 11: same as in lane 10, but subsequently cleaved with BsiEI
  Lane 12: G:T mismatched primer, amplification with Expand HiFi PCR System
  Lane 13: same as in lane 12, but subsequently cleaved with BsiEI
  Lane 14: G:T mismatched primer, amplification with Taq polymerase/Afu exonuclease III
  Lane 15: same as in lane 14, but subsequently cleaved with BsiEI
  Lane 16: G:T mismatched primer, amplification with Tgo DNA polymerase
  Lane 17: same as in lane 16, but subsequently cleaved with BsiEI
  Lane 18: DNA Molecular Weight Marker V
  Lane 19: DNA Molecular Weight Marker V Lane 20: G:C mismatched primer, amplification with Taq DNA polymerase Lane 21: same as in lane 20, but subsequently cleaved with BsiEI Lane 22: G:C mismatched primer, amplification with Expand HiFi PCR System Lane 23: same as in lane 22, but subsequently cleaved with BsiEI Lane 24: G:C mismatched primer, amplification with Taq polymerase/Afu exonuclease III Lane 25: same as in lane 24, but subsequently cleaved with BsiEI Lane 26: G:C mismatched primer, amplification with Tgo DNA polymerase Lane 27: same as in lane 26, but subsequently cleaved with BsiEI Lane 28: CG:AT mismatched primer, Taq DNA polymerase Lane 29: same as in lane 28, but subsequently cleaved with BsiEI Lane 30: CG:AT mismatched primer, Expand HiFi PCR System Lane 31: same as in lane 2, but subsequently cleaved with BsiEI Lane 32: CG:AT mismatched primer, Taq polymerase/Afu exonuclease III Lane 33: same as in lane 2, but subsequently cleaved with BsiEI Lane 34: CG:AT mismatched primer, amplification with Tgo DNA polymerase Lane 35: same as in lane 2, but subsequently cleaved with BsiEI Lane 36: DNA Molecular Weight Marker V.

PCR was carried out using 2.5 Units Taq DNA Polymerase (ROCHE Diagnostics GmbH, No. 1435094), 0.25 µg of *Archaeoglobus fulgidus* exonuclease III from Example IV, 10 ng of DNA from bacteriophage λ, 0.4 µM of each primer, 200 µM of dNTP's, 1.5 mM of $MgCl_2$, 50 mM of Tris-HCl, pH 9.2, 16 mM of $(NH_4)_2SO_4$. PCR was performed in an volume of 50 µl PCR with the following conditions:

1× 94° C., 2 min;
40× 94° C., 10 sec; 60° C., 30 sec; 72° C., 1 min;
1× 72° C., 7 min;

The function of the exonuclease/Taq polymerase mixture was compared to controls as 2.5 Units of Taq DNA polymerase, 0.3 Units of Tgo DNA polymerase (ROCHE Diagnostics GmbH) and to 0.75 µl of Expand™ High Fidelity PCR System (ROCHE Diagnostics GmbH, No.1732641). As indicated by successful digestion of the PCR products with BsiEI *A. fulgidus* exonuclease III showed correcting activity of all described mismatches with an effectivity of 90 to 100% (FIG. 5). Taq DNA Polymerase as expected showed no correcting activity, while Tgo DNA Polymerase with it's 3'–5'exonuclease activity corrected completely as well. The Expand™ High Fidelity PCR System showed only with the two base mismatch 100% correcting activity. The other mismatches were repaired with an effectivity of approximately 50%.

EXAMPLE VIII

Fidelity of Afu Exonuclease III DNA Polymerase Mixtures in the PCR Process

The fidelity of Afu exonuclease III/Taq DNA polymerase mixtures in the PCR process was determined in an assay based on the amplification, circularisation and transformation of the pUC19 derivate pUCIQ17, containing a functional lac $I^q$ allele (Frey, B. and Suppmann B. (1995) *Biochemica* 2:34–35). PCR-derived mutations in lac I are resulting in a derepression of the expression of lac Zα and subsequent formation of a functional β-galactosidase enzyme which can be easily detected on X-Gal indicator plates. The error rates of Taq polymerase/Afu exonuclease mixtures determined with this lac I-based PCR fidelity assay were determined in comparison to Taq DNA polymerase and Expand HiFi PCR System (Roche Molecular Biochemicals) and Pwo DNA polymerase (Roche Molecular Biochemicals) as controls.

The plasmid pUCIQ17 was linearized by digestion with DraII to serve as a substrate for PCR amplification with the enzymes tested.

Both of the primers used have ClaI sites at their 5 prime ends:
SEQ ID NO.: 8
Primer 1: 5'-AGCTTATCGATGGCACTTTTCGGG-GAAATGTGCG-3'
SEQ ID NO.: 9

Primer 2: 5'-AGCTTATCGATAAGCGGATGCCGG-GAGCAGACAAGC-3'

The length of the resulting PCR product is 3493 bp.

The PCR was performed in a final volume of 50 µl in the presence of 1.5 mM $MgCl_2$, 50 mM Tris⁻ HCl, pH 8.5 (25° C.), 12.5 mM $(NH_4)_2SO_4$, 35 mM KCl, 200 µM dNTPs and 2.5 units of Taq polymerase and 125 ng, 175 ng, 250 ng, 375 ng and 500 ng, respectively of Afu exonuclease III.

The cycle conditions were as follows:

1×denaturation of template for 2 min. at 95° C.

8× [denaturation at 95° C. for 10 sec.
annealing at 57° C. for 30 sec.
elongation at 72° C. for 4 min.]

16× [denaturation at 95° C. for 10 sec.
annealing at 57° C. for 30 sec.
elongation at 72° C. for 4 min.+
cycle elongation of 20 sec. for each cycle]

After PCR, the PCR products were PEG-precipitated (Barnes, W. M. (1992) *Gene* 112:229) the DNA restricted with ClaI and purified by agarose gel electrophoresis. The isolated DNA was ligated using the Rapid DNA Ligation Kit (Roche Molecular Biochemicals) and the ligation products transformed in *E. coli* DH5α, plated on TN Amp X-Gal plates. The α-complementing *E. coli* strain DH5α transformed with the resulting plasmid pUCIQ17 (3632 bp), shows white (lacI⁺) colonies on TN plates (1.5% Bacto Tryptone, 1% NaCl, 1.5% Agar) containing ampicillin (100 µg/ml) and X-Gal (0.004% w/v). Mutations result in blue colonies.

After incubation overnight at 37° C., blue and white colonies were counted. The error rate (f) per bp was calculated with a rearranged equation as published by Keohavong and Thilly (Keohavong, P. and Thilly, W. (1989) *PNAS USA* 86:9253):

$$f = -1 \text{ nF}/d\Delta b \text{ bp}$$

where F is the fraction of white colonies:

$$F = \text{white } (lacI+) \text{ colonies/total colony number;}$$

d is the number of DNA duplications:

$$2^d = \text{output DNA/input DNA;}$$

and b is the effective target size of the (1080 bp) lac I gene, which is 349 bp according to Provost et al. (Provost et al. (1993) *Mut. Res.* 288:133).

Figure 6B:
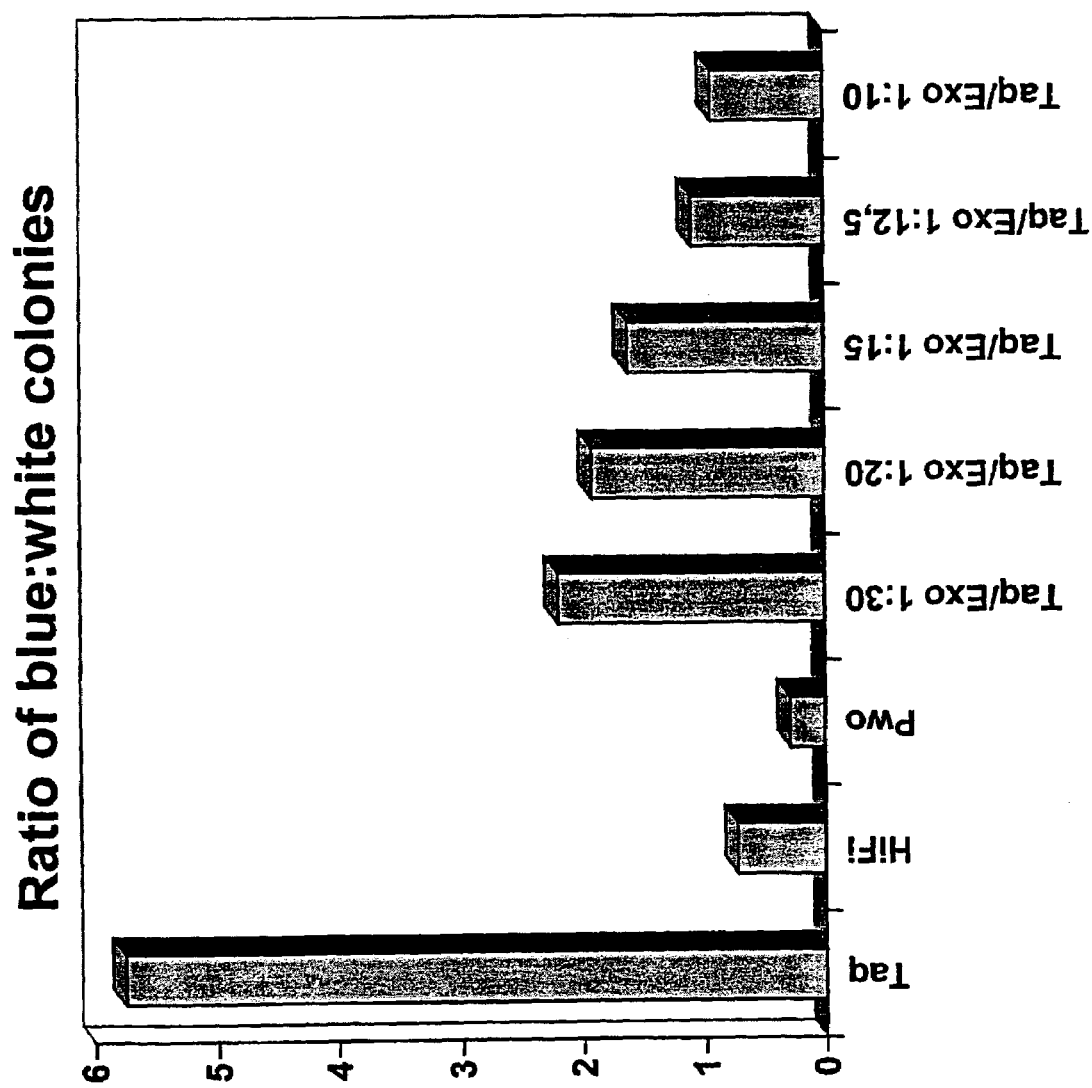
FIG. 6A.

The results shown in FIG. 6A and FIG. 6B demonstrate that the presence of thermostable exonuclease III in the reaction mixture results in lower error rates. Dependent on the ratio of polymerase to exonuclease the error rate is decreasing. The fidelity achieved with the most optimal Taq polymerase/Afu exonuclease III mixture ($4,44\times10^{-6}$) is in a similar range as that of the Taq/Pwo mixture (Expand HiFi; $2,06\times10^{-6}$). Evaluation of the optimal buffer conditions will further improve the fidelity. The ratio between polymerase and exonuclease has to be optimized. High amounts of exonuclease reduce product yield, apparently decreasing amplification efficiency (Taq/Exo 1:10 corresponding to 2.5 units of Taq polymerase and 500 ng of Afu exonuclease III).

The fidelity of this system may further be optimized using conventional skill in the art e.g. by altering the buffer components, optimizing the concentration of the individual components or changing the cycle conditions.

EXAMPLE IX

Incorporation of dUTP in the Presence of Afu Exonuclease III During PCR

The Afu exonuclease/Taq polymerase mixture was tested for DNA synthesis with TTP completely replaced by dUTP. Comparision of either TTP or dUTP incorporation was determinated in PCR using 2.5 Units of Taq DNA Polymerase, in presence of 0.125 µg, 0.25 µg, 0.375 µg and 0.5 µg of *Archaeoglobus fulgidus* exonuclease III from example IV on native human genomic DNA as template using the β-globin gene as target. The following primers were used:

forward: 5'-TGG TTG AAT TCA TAT ATC TTA GAG GGA GGG C-3' (SEQ ID NO.: 10)

reverse: 5'-TGT GTC TGC AGA AAA CAT CAA GGG TCC CAT A-3' (SEQ ID NO.: 11)

Figure 7:
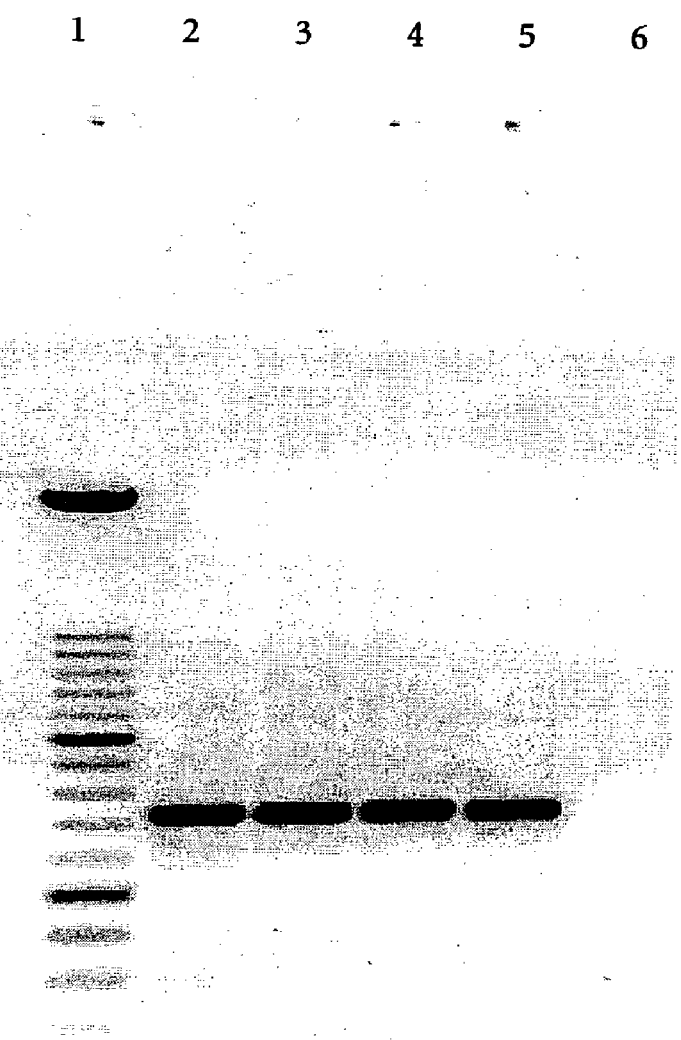
Figure 8:
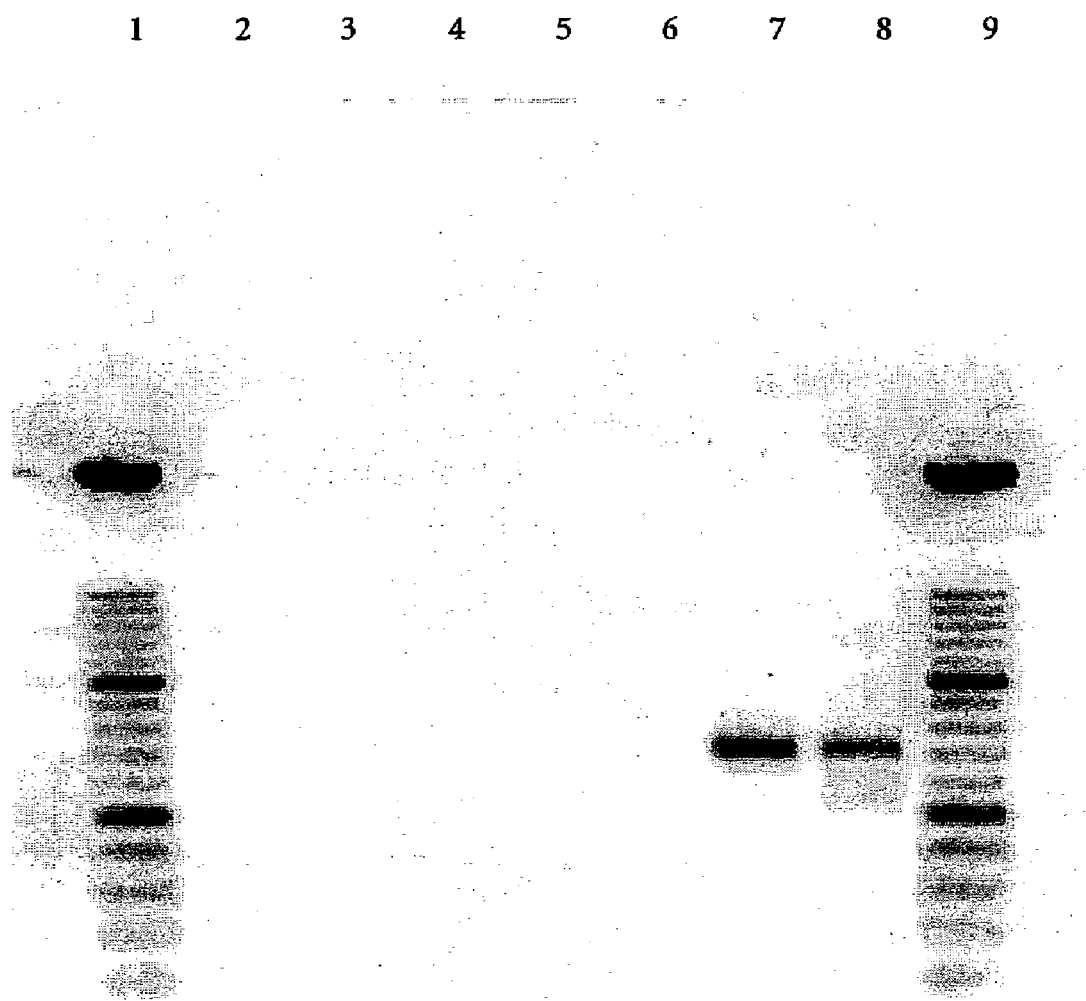

PCR was performed in 50 µL volume with the following cycle conditions:

1× 94° C., 2 nin;
40× 94° C., 10 sec; 60° C., 30 sec; 72° C., 1 min;
1× 72° C., 7 min;

Aliquots of the PCR reaction were separated on agarose gels. As shown in FIG. 7 with this template/primer system DNA synthesis in the presence of dUTP is possible with up to 375 ng of Afu exonuclease III. dUTP incorporation can further be proven by Uracil-DNA Glycosylase treatment (ROCHE Diagnostics GmbH, No.1775367) of aliquotes from the PCR reaction products for 30 min at ambient temperature and subsequent incubation for 5 min at 95° C. to cleave the polynucleotides at the apurinic sites which leads to complete degradation of the fragments. The analysis of the reaction products by agarose gel electrophoresis is shown in FIG. 8.

EXAMPLE X

Effect of Afu Exonuclease III on PCR Product Length

Taq polymerase is able to synthesize PCR products up to 3 kb in length on genomic templates. In order to estimate the capability of the Taq polymerase/Afu exonuclease mixture for the synthesis of longer products, the enzyme mixture was analyzed on human genomic DNA as template with three pairs of primers designed to amplifiy products of 9.3 kb, 12 kb and 15 kb length. The buffer systems used were from the Expand Long Template PCR System (Roche Molecular Biochemicals Cat. No 1 681 834). Reactions were performed in 50 µl volume with 250 ng of human genomic DNA, 220 ng of each primer, 350 µM of dNTPs and 2.5 units of Taq polymerase and 62,5 ng of Afu exonuclease with the conditions as outlined in Table 1:

TABLE 1

| Product length | Primers | Expand Long Template buffer No.: | PCR Programm |
|---|---|---|---|
| 9.3 kb | forward 7 reverse 14 | 1 | 1 × denat. at 94° C. for 2 min 10 × denat. at 94° C. for 10 sec. annealing at 65° C. for 30 sec elogation at 68° C. for 8 min. 20 × denat. at 94° C. for 10 sec. annealing at 65° C. for 30 sec elogation at 68° C. for 8 min. plus cycle elongation of 20 sec. per cycle 1 × elongation at 68° C. for 7 min. |

TABLE 1-continued

| Product length | Primers | Expand Long Template buffer No.: | PCR Programm |
|---|---|---|---|
| 12 kb | forward 1 reverse 3 | 2 | 1 × denat. at 94° C. for 2 min 10 × denat. at 94° C. for 10 sec. annealing at 62° C. for 30 sec elogation at 68° C. for 12 min. 20 × denat. at 94° C. for 10 sec. annealing at 62° C. for 30 sec elogation at 68° C. for 12 min. plus cycle elongation of 20 sec. per cycle 1 × elongation at 68° C. for 7 min. |
| 15 kb | forward 1 reverse 2 | 3 | same as for 12 kb |

The primer specific for amplification of the tPA genes used:

Primer 7a forward: 5'-GGA AGT ACA GCT CAG AGT TCT GCA GCA CCC CTG C-3' (SEQ ID NO.: 12)

Primer 14a reverse: 5'-CAA AGT CAT GCG GCC ATC GTT CAG ACA CAC C-3' (SEQ ID NO.: 13)

Primer 1 forward: 5'-CCT TCA CTG TCT GCC TAA CTC CTT CGT GTG TCC C-3' (SEQ ID NO.: 14)

Primer 2 reverse: 5'-ACT GTG CTT CCT GAC CCA TGG CAG AAG CGC CTT C-3' (SEQ ID NO.: 15)

Primer 3 reverse: 5'-CCT TCT AGA GTC AAC TCT AGA TGT GGA CTT AGA G-3' (SEQ ID NO.: 16)

Figure 9:
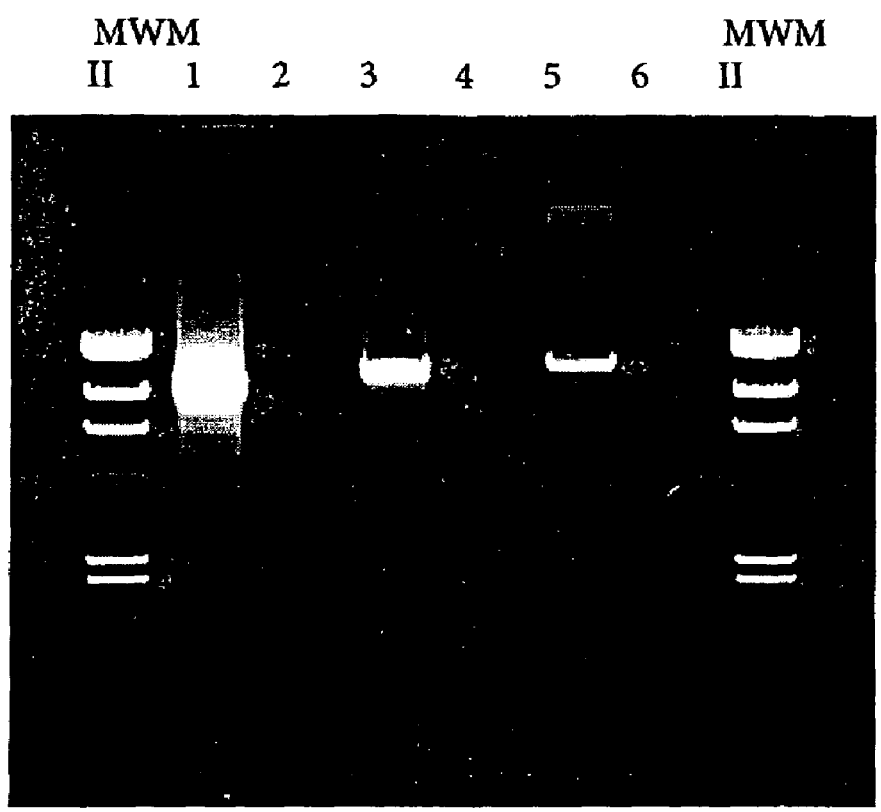

As shown in FIG. 9 it is possible to synthesize products of at least 15 kb in length with the Taq polymerase/Afu exonuclease mixture.

EXAMPLE XI

Thermostable Exonuclease III can be Replaced by a Polymerase Mutant with Reduced Polymerase Activity but Increased 3' Exonuclease-Activity DNA polymerase from Thermococcuss aggregans (Tag) described from Niehaus F., Frey B. and Antranikian G. in WO97/35988 or *Gene* (1997) 204 (1–2), 153–8, with an amino acid exchange at position 385 in which tyrosine was replaced by asparagine (Boehlke at al. submitted for publication and European patent application 00105 155.6) shows only 6.4% of the polymerase activity but 205% of the exonuclease activity of the wild type DNA polymerase. This enzyme was used to demonstrate that the invention is not restricted to exonuclease III-type enzymes but also includes other types of enzymes contributing 3' exonuclease activity.

Figure 10:
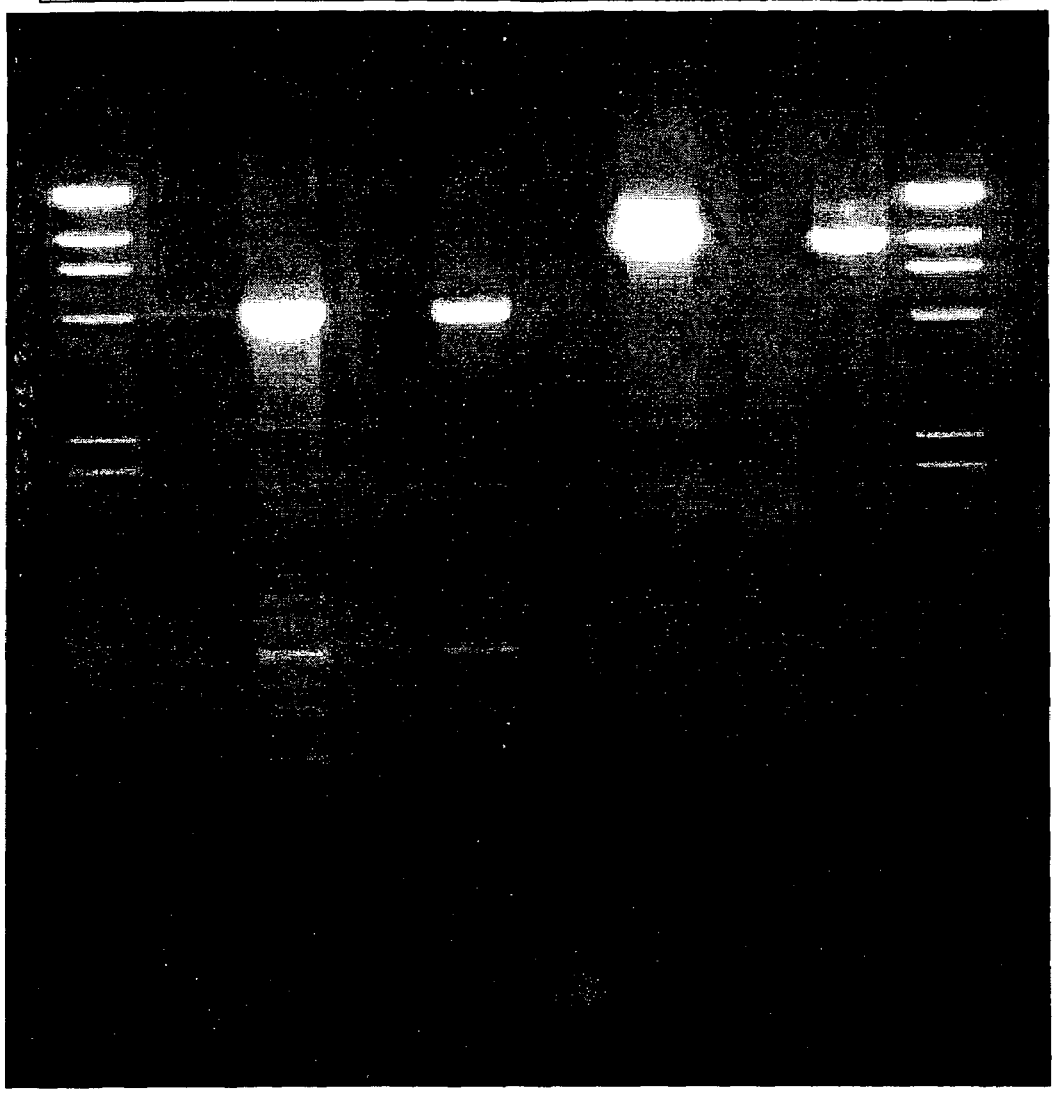

Reactions were performed in 50 µl volume with 200 ng of human genomic DNA, 200 µM dNTP, 220 ng of each primer and Expand HiFi buffer incl. Mg$^{++}$ for reactions 1–4 or Expand Long Template buffer 1 for reactions 5–8 (FIG. 10). In order to amplify a 4.8 kb fragment of the tPA gene, primer tPA 7a forward (5'-GGA AGT ACA GCT CAG AGT TCT GCA GCA CCC CTG C-3', SEQ ID NO.: 12) and tPA 10a reverse (5'-GAT GCG AAA CTG AGG CTG GCT GTA CTG TCT C-3', SEQ ID NO.: 17) were used in reactions 1–4. In order to amplify a 9.3 kb fragment of of the tPA gene, primer tPA 7a forward and tPA 14a reverse (5'-CAA AGT CAT GCG GCC ATC GTT CAG ACA CAC C-3', SEQ ID NO.: 13) were used in reactions 5–8. 2.5 units Taq polymerase were added to reactions 1, 2, 4, 5, 6, and 8, not to reactions 3 and 7 which were used as negative controls. 11 ng of Tag polymerase mutant were added to reactions 2, 3, 6 and 7, 150 ng of Afu Exonuclease III were added to reactions 4 and 8.

The cycle programs used for reactions 1–4:

1× 94° C., 2 min,

10× 94° C., 10 sec
62° C., 30 sec
68° C., 4 min

20× 94° C., 10 sec
62° C., 30 sec
68° C., 4 min, plus cycle elongation of 20 sec per cycle 1× 68° C. for 7 min for reactions 5–8:

1× 94° C., 2 min,

10× 94° C., 10 sec
65° C., 30 sec
68° C., 8 min

20× 94° C., 10 sec
65° C., 30 sec
68° C., 8 min, plus cycle elongation of 20 sec per cycle 1× 68° C. for 7 min The PCR products were analysed on a 1% agarose gel containg ethidium bromide (FIG. 10). The data show that Taq polymerase is able to amplify the 4.8 kb fragment but with low yield. The combination of Taq polymerase with Tag polymerase mutant or Afu Exo III results in a strong increase in product yield. The Tag polymerase mutant enzyme by itself is not able to synthesize this product.

Similar results were obtained with the 9.3 kb system. Using Taq polymerase alone no product is detectable. In combination with Tag polymerase mutant or Afu Exo III the expected PCR product is obtained in high yield.

These results show that Taq polymerase is not able to amplify DNA fragments of several kb from genomic DNA and support the hypothesis of Barnes (Barnes W. M. (1994) *Proc. Natl. Acad. Sci.* USA, 91:2216–2220) that the length limitation for PCR amplification is caused by low efficiency of extension at the sites of incorporation of mismatched base pairs. After removal of the mismatched nucleotide at the primer end, Taq polymerase is able to reassume DNA synthesis. The completed nucleic acid chain as a full length product can then serve as a template for primer binding in subsequent cycles.

EXAMPLE XII

Afu Exo III is not Active on Linear Single Stranded DNA

Reactions were performed in 50 µl volume with 270 ng of Afu Exo III, 5 µg of a 49-mer oligonucleotide in Expand HiFi PCR buffer with MgCl$_2$ and incubated for 0, 1, 2, 3, 4, and 5 hours at 65° C. After addition of 10 µl of Proteinase K solution (20 mg/ml) the samples were incubated for 20 min. at 37° C. The reaction products were analysed on a 3.5% Agarose gel containing ethidium bromide.

Figure 11:
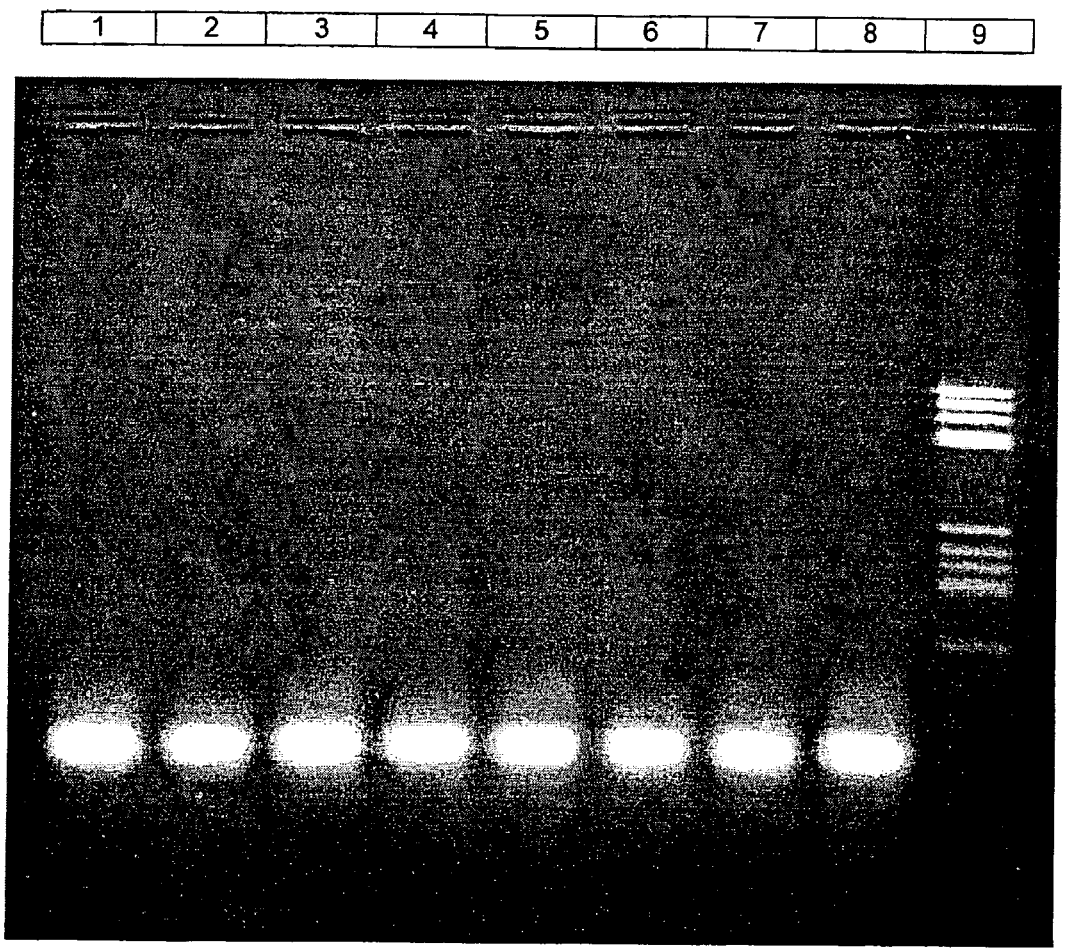

The result is depicted in FIG. 11. It showes that the nucleic acid has the same size in all lanes. The product obtained after incubation for up to 5 hours (lane 6) with Afu Exo III has the same size as the controls (lanes 1, 7 and 8). Neither a significant reduction in intensity of the full length oligonucleotide nor a smear deriving from degraded products can be observed.

EXAMPLE XIII

Comparison of Afu Exonuclease III with a Thermostable B-Type Polymerase in Primer Degradating Activity Thermostable B-type polymerases are reported to have single and double stranded nuclease activity (Kong H. et al. (1993) *Journal Biol. Chem.* 268:1965–1975). This activity is able to degrade primer molecules irrespective whether they are hybridized to the template or single stranded. The replacement of a thermostable B-type polymerase by a thermostable exonuclease in the reaction mixture might be of advantage with respect to stability of single stranded primer or other nuclei acids present in the reaction mixture.

In order to test for primer degrading activity, reaction mixtures without template DNA were incubated for 1 hour at 72° C., then DNA was added and PCR was performed. The results were compared with reactions containing Tgo polymerase as an example for a thermostable B-type polymerase (Angerer B. et al. WO 98/14590). As control the same mixtures were used without prior incubation. The results are summarized in Table 2.

TABLE 2

| reaction # | enzyme(s) | preincubation in the absence of template DNA | preinc. in the presence of nucleotides | second addition of primer after preincubaion |
|---|---|---|---|---|
| 1 | Tgo | yes | yes | |
| 2 | Tgo | yes | yes | |
| 3 | Tgo | no | | |
| 4 | Tgo | no | | |
| 5 | Tgo | yes | no | |
| 6 | Tgo | yes | no | |
| 7 | Tgo | no | | |
| 8 | Tgo | no | | |
| 9 | Tgo | yes | no | yes |
| 10 | Tgo | yes | no | yes |
| 11 | Taq | yes | yes | |
| 12 | Taq plus Afu Exo III | yes | yes | |
| 13 | Taq plus Afu Exo III | yes | yes | |
| 14 | Taq | no | | |
| 15 | Taq plus Afu Exo III | no | | |
| 16 | Taq plus Afu Exo III | no | | |

As target for amplification a fragment of the p53 gene was chosen, the primer used were: p5315'-GTC CCA AGC AAT GGA TGA T-3' (SEQ ID NO.: 18) and p53II 5'-TGG AAA CTT TCC ACT TGA T-3' (SEQ ID NO.: 19). PCR reactions were performed in 50 µl volume.

Reactions nos. 1–10 contained 200 ng of human genomic DNA, 40 pmole of each primer, 10 mM Tis-HCl, pH 8.5, 17.5 mM (NH$_4$)$_2$SO$_4$, 1.25 mM MgCl$_2$, 0.5% Tween, 2.5% DMSO, 250 µg/ml BSA and 1 unit (reactions number 1, 3, 5, 7 and 9) or 1.5 units (reactions number 2, 4, 6, 8 and 10) Tgo polymerase and 200 µM dNTPs.

Reactions number 11 to 16 contained 2.5 units Taq polymerase, Expand HiFi buffer with Mg$^{++}$, 40 pmoles of primer, 200 µM dNTPs, 100 ng human genomic DNA. Reactions number 12 and 15 contained 37.5 ng of Afu Exo III, reactions number 13 and 16 contained 75 ng of Afu Exo III.

As described in table 2 reactions 1, 2, 5, 6 and 11 to 13 were incubated for 1 hour at 72° C. in the absence of template DNA. The template DNA was added before PCR was started. Reactions 5, 6, 9 and 10 were preincubated in the absence of nucleotides, reactions 9 and 10 were supplemented with additional 40 pmoles of primer after the preincubation step. Because of the 5'-exonuclease activity of Taq polymerase, the enzyme was added after preincubation to reactions 11 to 13.

PCR conditions:

1× 94° C., 2 min

35× 94° C., 10 sec
55° C., 30 sec
72° C., 4 min

1× 72° C. for 10 min

Figure 12:
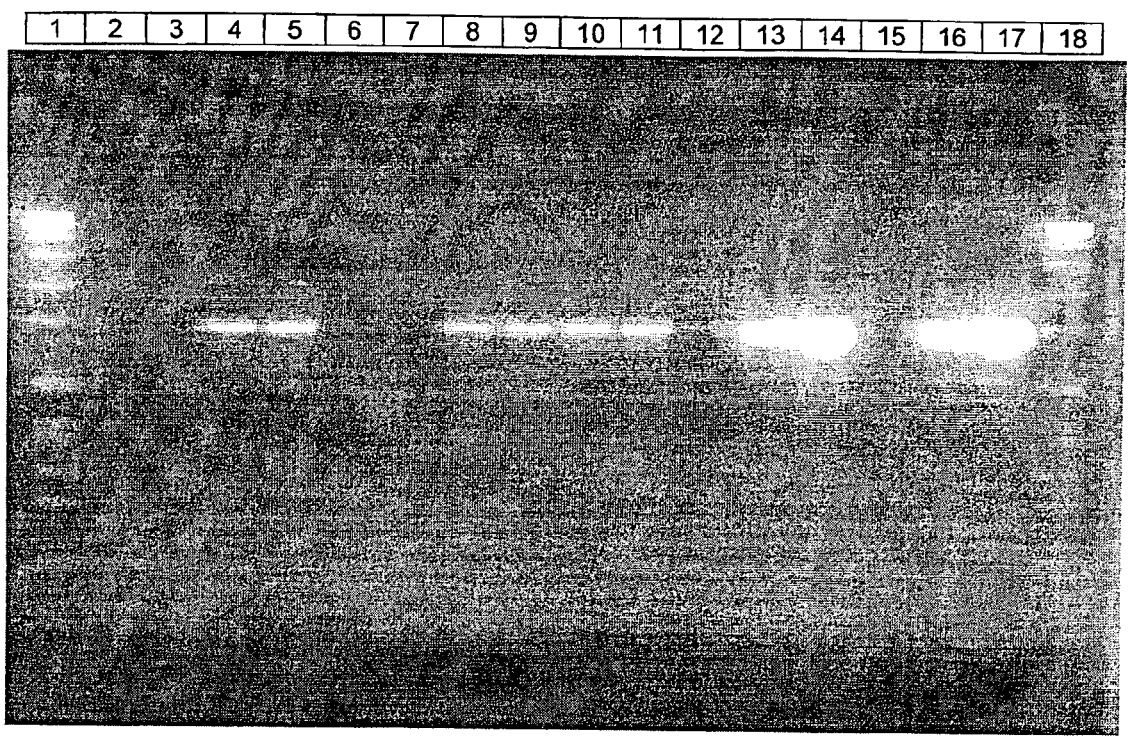

The reaction products were analysed on an agarose gel and stained with ethidium bromide (FIG. 12).

When Tgo polymerase was incubated with the primer in the absence of template DNA (reactions 1, 2, 5 and 6) and compared with the corresponding reactions without preincubation (3, 4, 7 and 8) a clear difference was observed. The preincubation results in strongly reduced PCR product obviously affecting at least one essential component, most probably the PCR primer. Extra addition of 40 pmoles of PCR primer (reactions 9 and 10) after the preincubation step results in strong signals with intensities comparable to the control reaction which were not preincubated. This shows that Tgo polymerase, a thermostable B-type polymerase, degrades PCR primer in the absence of template no matter whether dNTPs are present or not.

The PCR products obtained with reactions 12 and 13, in which the primer were preincubated with Afu Exonuclease III before addition of template DNA and Taq polymerase gave similar bands as those obtained with reactions 15 and 16, in which no preincubation step was used. From the similar strong band intensities it can be concluded that little or no degradation of primer occured and that single stranded oligonucleotides are poor substrates for Afu Exonuclease III. From the strong band intensities or enhanced yields of PCR products it can be concluded that the enzyme enhances fidelity of an amplification process.

The invention claimed is:

1. A composition comprising a first thermostable *Archeoglobus fulgidus* enzyme exhibiting 3'–5' exonuclease activity but essentially no DNA polymerase activity and a second enzyme exhibiting DNA polymerase activity, wherein said first thermostable *Archeoglobus fulgidus* enzyme is active under the incubation and temperature conditions of a polymerase chain reaction and is encoded by DNA which hybridizes to a primer having a sequence as shown in SEQ ID NO: 1 and a primer having a sequence as shown in SEQ ID NO: 2, said composition enhancing the fidelity of an amplification process in comparison to the use of the single second enzyme.

2. The composition according to claim 1 wherein the second enzyme is lacking proofreading activity.

3. The composition according to claim 2 wherein the second enzyme is Taq polymerase.

4. The composition of claim 1, wherein the first thermostable *Archeoglobus fulgidus* enzyme is SEQ ID NO: 18.

* * * * *

SEQUENCE LISTING

<160> NUMBER OF SEQ ID NOS: 18

<210> SEQ ID NO 1
<211> LENGTH: 31
<212> TYPE: DNA
<213> ORGANISM: Artificial Sequence
<220> FEATURE:
<223> OTHER INFORMATION: Amplification Primer

<400> SEQUENCE: 1
gaaacgagga tccatgctcaa aatcgccacc                               31

<210> SEQ ID NO 2
<211> LENGTH: 31
<212> TYPE: DNA
<213> ORGANISM: Artificial Sequence
<220> FEATURE:
<223> OTHER INFORMATION: Amplification Primer

<400> SEQUENCE: 2
ttgttcactg cagctacacg tcaaacacag c                              31

<210> SEQ ID NO 3
<211> LENGTH: 23
<212> TYPE: DNA
<213> ORGANISM: Artificial Sequence
<220> FEATURE:
<223> OTHER INFORMATION: Amplification Primer

<400> SEQUENCE: 3
ggttatcgaa atcagccaca gcg                                       23

<210> SEQ ID NO 4
<211> LENGTH: 27
<212> TYPE: DNA
<213> ORGANISM: Artificial Sequence
<220> FEATURE:
<223> OTHER INFORMATION: Amplification Primer

<400> SEQUENCE: 4
tggatacgtc tgaactggtc acggtca                                   27

```
<210> SEQ ID NO 5
<211> LENGTH: 27
<212> TYPE: DNA
<213> ORGANISM: Artificial Sequence
<220> FEATURE:
<223> OTHER INFORMATION: Amplification Primer

<400> SEQUENCE: 5
tggatacgtc tgaactggtc acggtct                                       27

<210> SEQ ID NO 6
<211> LENGTH: 27
<212> TYPE: DNA
<213> ORGANISM: Artificial Sequence
<220> FEATURE:
<223> OTHER INFORMATION: Amplification Primer

<400> SEQUENCE: 6
tggatacgtc tgaactggtc acggtcc                                       27

<210> SEQ ID NO 7
<211> LENGTH: 27
<212> TYPE: DNA
<213> ORGANISM: Artificial Sequence
<220> FEATURE:
<223> OTHER INFORMATION: Amplification Primer

<400> SEQUENCE: 7
tggatacgtc tgaactggtc acggtat                                       27

<210> SEQ ID NO 8
<211> LENGTH: 34
<212> TYPE: DNA
<213> ORGANISM: Artificial Sequence
<220> FEATURE:
<223> OTHER INFORMATION: Amplification Primer

<400> SEQUENCE: 8
agcttatcga tggcacttttc ggggaaatgt gcg                               34

<210> SEQ ID NO 9
<211> LENGTH: 36
<212> TYPE: DNA
<213> ORGANISM: Artificial Sequence
<220> FEATURE:
<223> OTHER INFORMATION: Amplification Primer

<400> SEQUENCE: 9
agcttatcga taagcggatg ccgggagcag acaagc                             36

<210> SEQ ID NO 10
<211> LENGTH: 31
<212> TYPE: DNA
<213> ORGANISM: Artificial Sequence
<220> FEATURE:
<223> OTHER INFORMATION: Amplification Primer

<400> SEQUENCE: 10
tggttgaatt catatatctt agagggaggg c                                  31

<210> SEQ ID NO 11
<211> LENGTH: 31
<212> TYPE: DNA
<213> ORGANISM: Artificial Sequence
<220> FEATURE:
<223> OTHER INFORMATION: Amplification Primer
```

-continued

```
<400> SEQUENCE: 11
tgtgtctgca gaaaacatca agggtcccat a                                   31

<210> SEQ ID NO 12
<211> LENGTH: 34
<212> TYPE: DNA
<213> ORGANISM: Artificial Sequence
<220> FEATURE:
<223> OTHER INFORMATION: Amplification Primer

<400> SEQUENCE: 12
ggaagtacag ctcagagttc tgcagcaccc ctgc                                34

<210> SEQ ID NO 13
<211> LENGTH: 31
<212> TYPE: DNA
<213> ORGANISM: Artificial Sequence
<220> FEATURE:
<223> OTHER INFORMATION: Amplification Primer

<400> SEQUENCE: 13
caaagtcatg cggccatcgt tcagacacac c                                   31

<210> SEQ ID NO 14
<211> LENGTH: 34
<212> TYPE: DNA
<213> ORGANISM: Artificial Sequence
<220> FEATURE:
<223> OTHER INFORMATION: Amplification Primer

<400> SEQUENCE: 14
ccttcactgt ctgcctaact ccttcgtgtg tccc                                34

<210> SEQ ID NO 15
<211> LENGTH: 34
<212> TYPE: DNA
<213> ORGANISM: Artificial Sequence
<220> FEATURE:
<223> OTHER INFORMATION: Amplification Primer

<400> SEQUENCE: 15
actgtgcttc ctgacccatg gcagaagcgc cttc                                34

<210> SEQ ID NO 16
<211> LENGTH: 34
<212> TYPE: DNA
<213> ORGANISM: Artificial Sequence
<220> FEATURE:
<223> OTHER INFORMATION: Amplification Primer

<400> SEQUENCE: 16
ccttctagag tcaactctag atgtggactt agag                                34

<210> SEQ ID NO 17
<211> LENGTH: 774
<212> TYPE: DNA
<213> ORGANISM: Archaeoglobus fulgidus
<220> FEATURE:
<221> NAME/KEY: CDS
<222> LOCATION: (1)..(774)
<223> OTHER INFORMATION:

<400> SEQUENCE: 17 atg ctc aaa atc gcc acc ttc aac gta aac tcc atc agg agc aga ctg    48
Met Leu Lys Ile Ala Thr Phe Asn Val Asn Ser Ile Arg Ser Arg Leu
```

```
                1               5                      10                          15
cac atc gtg att ccg tgg ctg aag gag aac aag cct gac att cta tgc        96
His Ile Val Ile Pro Trp Leu Lys Glu Asn Lys Pro Asp Ile Leu Cys
                    20                     25                       30 atg cag gag acg aag gtt gag aac agg aag ttt cct gag gcc gat ttt       144
Met Gln Glu Thr Lys Val Glu Asn Arg Lys Phe Pro Glu Ala Asp Phe
             35                    40                       45 cac cgc atc ggc tac cac gtc gtc ttc agc ggg agc aag gga agg aat       192
His Arg Ile Gly Tyr His Val Val Phe Ser Gly Ser Lys Gly Arg Asn
         50                    55                       60 gga gtg gcc ata gct tcc ctc gaa gag cct gag gat gtc agc ttc ggt       240
Gly Val Ala Ile Ala Ser Leu Glu Glu Pro Glu Asp Val Ser Phe Gly
 65                    70                       75                       80 ctc gat tca gag ccg aag gac gag gac agg ctg ata agg gca aag ata       288
Leu Asp Ser Glu Pro Lys Asp Glu Asp Arg Leu Ile Arg Ala Lys Ile
                     85                       90                       95 gct ggc ata gac gtg att aac acc tac gtt cct cag gga ttc aaa att       336
Ala Gly Ile Asp Val Ile Asn Thr Tyr Val Pro Gln Gly Phe Lys Ile
                    100                      105                     110 gac agc gag aag tac cag tac aag ctc cag tgg ctt gag agg ctt tac       384
Asp Ser Glu Lys Tyr Gln Tyr Lys Leu Gln Trp Leu Glu Arg Leu Tyr
                115                      120                      125 cat tac ctt caa aaa acc gtt gac ttc aga agc ttt gct gtt tgg tgt       432
His Tyr Leu Gln Lys Thr Val Asp Phe Arg Ser Phe Ala Val Trp Cys
            130                      135                      140 gga gac atg aac gtt gct cct gag cca atc gac gtt cac tcc cca gac       480
Gly Asp Met Asn Val Ala Pro Glu Pro Ile Asp Val His Ser Pro Asp
145                      150                      155                      160 aag ctg aag aac cac gtc tgc ttc cac gag gat gcg aga agg gca tac       528
Lys Leu Lys Asn His Val Cys Phe His Glu Asp Ala Arg Arg Ala Tyr
                    165                      170                      175 aaa aaa ata ctc gaa ctc ggc ttt gtt gac gtg ctg aga aaa ata cat       576
Lys Lys Ile Leu Glu Leu Gly Phe Val Asp Val Leu Arg Lys Ile His
                180                      185                      190 ccc aac gag aga att tac acc ttc tac gac tac agg gtt aag gga gcc       624
Pro Asn Glu Arg Ile Tyr Thr Phe Tyr Asp Tyr Arg Val Lys Gly Ala
            195                      200                      205 att gag cgg ggg ctg gga tgg agg gtt gat gcc atc ctc gcc acc cca       672
Ile Glu Arg Gly Leu Gly Trp Arg Val Asp Ala Ile Leu Ala Thr Pro
        210                      215                      220 ccc ctc gcc gaa aga tgc gtg gac tgc tac gca gac atc aaa ccg agg       720
Pro Leu Ala Glu Arg Cys Val Asp Cys Tyr Ala Asp Ile Lys Pro Arg
225                      230                      235                      240 ctg gca gaa aag cca tcc gac cac ctc cct ctc gtt gct gtg ttt gac       768
Leu Ala Glu Lys Pro Ser Asp His Leu Pro Leu Val Ala Val Phe Asp
                    245                      250                      255 gtg tag                                                                774
Val
```

<210> SEQ ID NO 18
<211> LENGTH: 257
<212> TYPE: PRT
<213> ORGANISM: Archaeoglobus fulgidus

<400> SEQUENCE: 18

```
Met Leu Lys Ile Ala Thr Phe Asn Val Asn Ser Ile Arg Ser Arg Leu
 1               5                  10                  15

His Ile Val Ile Pro Trp Leu Lys Glu Asn Lys Pro Asp Ile Leu Cys
            20                  25                  30
```

-continued

```
Met Gln Glu Thr Lys Val Glu Asn Arg Lys Phe Pro Glu Ala Asp Phe
         35                  40                  45

His Arg Ile Gly Tyr His Val Val Phe Ser Gly Ser Lys Gly Arg Asn
     50                  55                  60

Gly Val Ala Ile Ala Ser Leu Glu Glu Pro Glu Asp Val Ser Phe Gly
 65              70                  75                      80

Leu Asp Ser Glu Pro Lys Asp Glu Asp Arg Leu Ile Arg Ala Lys Ile
             85                      90                  95

Ala Gly Ile Asp Val Ile Asn Thr Tyr Val Pro Gln Gly Phe Lys Ile
             100                 105                 110

Asp Ser Glu Lys Tyr Gln Tyr Lys Leu Gln Trp Leu Glu Arg Leu Tyr
         115                 120                 125

His Tyr Leu Gln Lys Thr Val Asp Phe Arg Ser Phe Ala Val Trp Cys
     130                 135                 140

Gly Asp Met Asn Val Ala Pro Glu Pro Ile Asp Val His Ser Pro Asp
 145             150                 155                     160

Lys Leu Lys Asn His Val Cys Phe His Glu Asp Ala Arg Arg Ala Tyr
             165                 170                 175

Lys Lys Ile Leu Glu Leu Gly Phe Val Asp Val Leu Arg Lys Ile His
             180                 185                 190

Pro Asn Glu Arg Ile Tyr Thr Phe Tyr Asp Tyr Arg Val Lys Gly Ala
         195                 200                 205

Ile Glu Arg Gly Leu Gly Trp Arg Val Asp Ala Ile Leu Ala Thr Pro
     210                 215                 220

Pro Leu Ala Glu Arg Cys Val Asp Cys Tyr Ala Asp Ile Lys Pro Arg
 225             230                 235                     240

Leu Ala Glu Lys Pro Ser Asp His Leu Pro Leu Val Ala Val Phe Asp
             245                 250                 255

Val
```